United States Patent
Wang

(10) Patent No.: US 11,185,485 B2
(45) Date of Patent: Nov. 30, 2021

(54) HAIR COLORING COMPOSITIONS AND METHODS OF USING THE SAME

(71) Applicant: L'OREAL, Paris (FR)

(72) Inventor: Jeffrey Wang, Jersey City, NJ (US)

(73) Assignee: L'OREAL, Paris (FR)

(*) Notice: Subject to any disclaimer, the term of this patent is extended or adjusted under 35 U.S.C. 154(b) by 0 days.

(21) Appl. No.: 16/885,498

(22) Filed: May 28, 2020

(65) Prior Publication Data
US 2020/0375865 A1 Dec. 3, 2020

Related U.S. Application Data

(60) Provisional application No. 62/855,215, filed on May 31, 2019.

(51) Int. Cl.
| | | |
|---|---|---|
| *A61Q 5/10* | (2006.01) | |
| *A61K 8/44* | (2006.01) | |
| *A61K 8/60* | (2006.01) | |
| *A61K 8/34* | (2006.01) | |
| *A61K 8/49* | (2006.01) | |

(52) U.S. Cl.
CPC ............... *A61K 8/44* (2013.01); *A61K 8/345* (2013.01); *A61K 8/4973* (2013.01); *A61K 8/604* (2013.01); *A61K 2800/10* (2013.01); *A61K 2800/4322* (2013.01); *A61K 2800/882* (2013.01)

(58) Field of Classification Search
CPC . A61Q 5/10; A61K 8/22; A61K 8/411; A61K 8/4926; A61K 8/415; A61K 8/342; A61K 2800/4324; A61K 2800/88; A61K 2800/882; A61K 8/3347; A61K 8/44; A61K 8/39; A61K 8/416; A61K 8/34; A61K 8/37; A61K 2800/5426; A61K 8/604; A61K 8/06; A61K 8/062; A61K 8/602; A61K 2800/5422; A61K 2800/5424; A61K 2800/262; A61K 47/14; A61K 31/13
USPC ............................................................ 8/405
See application file for complete search history.

(56) References Cited

U.S. PATENT DOCUMENTS

| | | |
|---|---|---|
| 6,572,663 B1* | 6/2003 | Pitfield ................. A61K 8/068 8/405 |
| 6,669,933 B2 | 12/2003 | Duffer et al. |
| 7,306,633 B2 | 12/2007 | Wilz |
| 8,231,690 B2 | 7/2012 | Lalleman et al. |
| 8,425,622 B2 | 4/2013 | Felts et al. |
| 8,439,981 B2 | 5/2013 | Felts et al. |
| 9,066,859 B1 | 6/2015 | Rizk et al. |
| 9,326,585 B2 | 5/2016 | Uellner |
| 2002/0035758 A1 | 3/2002 | Pratt |
| 2002/0124329 A1 | 9/2002 | Pratt |
| 2003/0028979 A1 | 2/2003 | Duffer et al. |
| 2003/0061668 A1* | 4/2003 | Sander ..................... A61K 8/39 8/405 |
| 2003/0145393 A1* | 8/2003 | Corbella ................ A61K 8/736 8/405 |
| 2005/0210606 A1 | 9/2005 | Wilz |
| 2006/0117498 A1* | 6/2006 | Bureiko ................. A61K 8/556 8/406 |
| 2007/0209124 A1* | 9/2007 | Bureiko ................... A61K 8/44 8/405 |
| 2011/0048446 A1 | 3/2011 | Torgerson et al. |
| 2011/0297172 A1 | 8/2011 | Lalleman et al. |
| 2011/0236324 A1 | 9/2011 | Deo |
| 2012/0128601 A1* | 5/2012 | Behler ................... A61K 8/062 424/59 |
| 2012/0297556 A1 | 11/2012 | Felts et al. |
| 2012/0301412 A1 | 11/2012 | Felts et al. |
| 2013/0129648 A1 | 5/2013 | Nguyen et al. |
| 2015/0136168 A1 | 5/2015 | Uellner |
| 2020/0038299 A1 | 2/2020 | Hitchcock-Agostino et al. |

* cited by examiner

*Primary Examiner* — Eisa B Elhilo
(74) *Attorney, Agent, or Firm* — Polsinelli PC

(57) ABSTRACT

Hair coloring compositions that form a transparent microemulsion and have a desirable texture. The hair coloring compositions may include about 0.1 to about 10 wt. % of one or more oxidative dye precursors; about 0.1 to about 15 wt. % of one or more anionic surfactants chosen from acyl amino acid surfactants; about 0.1 to about 15 wt. % of one or more amphoteric surfactants; about 0.1 to about 30 wt. % of a plurality of nonionic surfactants; and water. The plurality of nonionic surfactants include about 0.1 to about 15 wt. % of one or more alkyl polyglucosides; about 0.1 to about 15 wt. % of a sorbitan compound, a derivative thereof, or a mixture thereof; and about 0.1 to about 10 wt. % of one or more polyol esters.

20 Claims, No Drawings

HAIR COLORING COMPOSITIONS AND METHODS OF USING THE SAME

CROSS-REFERENCE TO RELATED APPLICATIONS

This application claims the benefit under 35 U.S.C. § 119(e) of the filing date of U.S. Provisional Patent Application No. 62/855,215, filed on May 31, 2019, the entirety of which is herein incorporated by reference.

FIELD OF THE INVENTION

The present disclosure relates to hair coloring compositions, and particularly to hair coloring compositions in the form of a transparent microemulsion, that have a desirable texture. Methods of making and using such hair coloring compositions are also disclosed herein.

BACKGROUND OF THE INVENTION

It is known that consumers desire to use cosmetic and care compositions that enhance the appearance of keratinous substrates such as hair, e.g., by changing the color, style, and/or shape of the hair, and/or by imparting various properties to hair, such as shine and conditioning. Many of the known compositions and processes for enhancing the appearance of the hair involve the chemical treatment of the hair.

The process of changing the color of hair, for example, can involve depositing an artificial color onto the hair that provides a different shade or color to the hair, and/or lifting color from the hair, such as lightening the color of dark hair to lighter shades. The process of lifting the color of hair, also known as lightening, generally requires the use of compositions that comprise at least one oxidizing agent.

Imparting a color change or color effect to hair can be done using permanent, semi-permanent, and temporary hair coloring products. Many permanent hair coloring products use oxidative hair color that bleaches the melanin found in the hair shaft as well as imparts color. Activated peroxide in the oxidative dye composition provides a bleaching effect while the oxidative dye molecules penetrate the hair shaft and polymerize therein. While hair that is oxidatively colored provides a certain permanence, re-coloring every four to six weeks may be necessary due to new hair growth. Oxidative hair color is sold in the form of a two component kit. The reactivity of the oxidative dye and the oxidizing agent means that the two ingredients cannot be formulated into a single composition. Rather, the kits have one container filled with an aqueous composition that contains the oxidative dyes and a second container filled with a developer composition that contains an oxidizing agent, usually hydrogen peroxide. The two containers are combined immediately prior to use and applied to hair. The oxidizing agent and dyes react when mixed. The mixture is applied to hair for an appropriate period of time, generally 20 to 60 minutes, then rinsed off with water. Permanent hair color is very versatile and long lasting in the colors and effects it provides, and it is only with permanent hair color that one can color hair to a shade that is lighter than the natural color.

Semi-permanent hair color generally provides more lasting color than temporary dyes but without the permanence and commitment of oxidative color. Semi-permanent color is a single component product containing direct dyes. Many of such products contain two types of dyes: one of smaller molecular size that are capable of penetrating the hair shaft and being retained within. While smaller molecular size permits these dyes to more easily penetrate the hair shaft. The second type of dye used in semi-permanent hair color has a larger molecular size and is too large to penetrate the hair shaft of normal virgin hair. However, such larger dye molecules easily penetrate porous and damaged hair where they are often retained due to their larger size. Accordingly, the balancing of the small and large dye molecules found in many semi-permanent products provides color with a uniform and durable effect. Semi-permanent color provides excellent gray blending and good color retention.

Temporary hair color may employ pigments and natural colorants (e.g., vegetable-derived) is often found in the rinse form, and typically lasts for one shampoo. Such hair color is often used when special effects are desired. Temporary color simply coats the hair shaft with colorants that are too large to penetrate its outer surface. Minor penetration of the hair shaft may occur in individuals with damaged or porous hair, but such color application rarely lasts through more than one or two shampoos.

SUMMARY OF THE DISCLOSURE

The instant disclosure relates to hair coloring compositions, and particularly hair coloring compositions in the form of a microemulsion, that have a desirable texture. The hair coloring compositions disclosed herein are formulated to provide rare, unique, and/or exquisite tactile impression. For example, aspects of the disclosure relate to the hair coloring compositions form microemulsions that can provide a glassy and/or slippery liquid impression. In some instances, the hair coloring compositions provide a texture that is commonly associated with the tactile impression of crushed ice.

The hair coloring compositions typically in include:
(a) about 0.1 to about 10 wt. % of one or more oxidative dye precursors;
(b) about 0.1 to about 15 wt. % of one or more anionic surfactants chosen from acyl amino acid surfactants;
(c) about 0.1 to about 15 wt. % of one or more amphoteric surfactants;
(d) about 0.1 to about 30 wt. % of a plurality of nonionic surfactants, the plurality of nonionic surfactants comprising:
  (i) about 0.1 to about 15 wt. % of one or more alkyl polyglucosides,
  (ii) about 0.1 to about 15 wt. % of one or more sorbitan derivatives, and
  (iii) about 0.1 to about 10 wt. % of one or more polyol esters; and
(e) water.

The hair coloring compositions may include aclyl amino acid surfactants that are chosen from acyl sarcosinates, acyl taurates, acyl glycinates, acyl glutamates, salts thereof, and a mixture thereof. In some instances, the acyl amino acid surfactants may be chosen from acyl glycinates.

Non-limiting examples of acyl glycinates include those chosen from sodium cocoyl glycinate, sodium lauroyl glycinate, sodium myristoyl glycinate, potassium lauroyl glycinate, potassium cocoyl glycinate, and a mixture thereof.

The one or more the one or more amphoteric surfactants may be chosen from betaines, alkyl sultaines, alkyl amphoacetates, alkyl amphoprorionates, salts thereof, and a mixture thereof. For example, the one or more amphoteric surfactants may include one or more betaines. Suitable betaines may, in some instances, be chosen from coco betaine, cocamidopropyl betaine, lauryl betaine, laurylhy-"

droxy sulfobetaine, lauryldimethyl betaine, cocamidopropyl hydroxysultaine, behenyl betaine, capryl/capramidopropyl betaine, lauryl hydroxysultaine, stearyl betaine, and mixtures thereof.

The plurality of nonionic surfactants includes at least one or more alkyl polyglucosides, one or more sorbitan derivatives, and one or more polyol esters. Non-limiting examples of the one or more alkyl polyglucosides that may incorporated in the hair coloring composition include those chosen from lauryl glucoside, octyl glucoside, decyl glucoside, coco glucoside, caprylyl/capryl glucoside, sodium lauryl glucose carboxylate, and a mixture thereof.

Suitable sorbitan derivatives include those chosen from polysorbate-20 (POE(20) sorbitan monolaurate), polysorbate-21 (POE(4) sorbitan monolaurate), polysorbate-40 (POE(20) sorbitan monopalmitate), polysorbate-60 (POE (20) sorbitan monostearate), polysorbate-61 (POE(4) sorbitan monostearate), polysorbate-65 (POE(20) sorbitan tristearate), polysorbate-80 (POE(20)sorbitan monooleate), polysorbate-81 (POE(4) sorbitan monooleate), polysorbate 85 (POE(20) Sorbitan Trioleate), sorbitan isostearate, sorbitan monolaurate, sorbitan monooleate, sorbitan monopalmitate, sorbitan monostearate, sorbitan sesquioleate, sorbitan trioleate and sorbitan tristearate and a mixture thereof. In some instances, the one or more sorbitan derivatives comprises polysorbate-21.

Non-limiting examples of the one or more polyol esters of the plurality of nonionic surfactants include those chosen from alkoxylated polyol esters. For instance, the alkoxylated polyol esters may be chosen from pegylated derivatives of propylene glycol oleate, propylene glycol caprylate/caprate, propylene glycol cocoate, propylene glycol stearate, and a mixture thereof. In some instances, the alkoxylated polyol esters are chosen from PEG-55 propylene glycol oleate, PEG-6 propylene glycol caprylate/caprate, PEG-8 propylene glycol cocoate, PEG-25 propylene glycol stearate, and PEG-120 propylene glycol stearate, and a mixture thereof.

Additionally, the hair coloring compositions may include one or more water-soluble solvents. For example, the one or more water-soluble solvents may include those chosen from glycols, C1-6 alcohols, glycerin, and a mixture thereof. In some instances, one or more glycols may be chosen from ethylene glycol, propylene glycol, butylene glycol, hexylene glycol, pentylene glycol, diethylene glycol, dipropylene glycol, 1,3 propanediol, glycerin, and a mixture thereof.

The hair coloring compositions may also include one or more alkalizing agents chosen from alkali metal carbonates, alkali metal phosphates, organic amines, hydroxide base compounds, and mixtures thereof. In some instances, the one or more alkalizing agents are chosen from ammonium hydroxide, ethanolamine and mixtures thereof.

In some instances, the hair coloring composition may include one or more cationic conditioning polymers, such as those chosen from polyquaterniums. In one example, the cationic conditioning polymer is polyquaternium-6. Additionally or alternatively, the hair coloring compositions may be formulated to be essentially free of sulfate based anionic surfactants. The hair coloring composition may have a viscosity of 10 mPa·s to about 10,000 mPa·s at 25° C. In some instances, the hair coloring compositions form a microemulsion that is transparent.

The hair coloring compositions may be provided in a kit by, e.g., a kit comprising an aqueous developer composition comprising a peroxide and the hair coloring composition. According to certain embodiments, however, the hair coloring composition may be provided and/or offered as an individual item.

In accordance with another aspect of the instant disclosure, provided is a method for coloring hair. The method for coloring hair includes mixing a hair coloring composition with an aqueous developer; applying the mixture onto hair and allowing the mixture to remain on the hair for about 1 to about 45 minutes; and rinsing the mixture from hair.

DETAILED DESCRIPTION OF THE DISCLOSURE

The instant disclosure relates to hair coloring compositions, and particularly hair coloring compositions in the form of a microemulsion, that have a unique texture. For example, the hair coloring compositions typically have a slippery liquid tactile impression and/or the tactile impression of crushed ice.

The hair coloring compositions typically form a microemulsion and include:
(a) about 0.1 to about 10 wt. % of one or more oxidative dye precursors;
(b) about 0.1 to about 15 wt. % of one or more anionic surfactants chosen from acyl amino acid surfactants;
(c) about 0.1 to about 15 wt. % of one or more amphoteric surfactants;
(d) about 0.1 to about 30 wt. % of a plurality of nonionic surfactants, the plurality of nonionic surfactants comprising:
 (i) about 0.1 to about 15 wt. % of one or more alkyl polyglucosides,
 (ii) about 0.1 to about 15 wt. % of a sorbitan compound, a derivative thereof, or a mixture thereof, and
 (iii) about 0.1 to about 10 wt. % of one or more polyol esters; and
(e) water.

The hair coloring compositions of the instance disclosure typically form an oil-in-water microemulsion, but may alternatively form a water-in-oil microemulsion. The microemulsions formed from the hair coloring compositions are preferably transparent and/or translucent. As used herein, the term "translucent" refers to the characteristic of a composition to permit the passage of light but does not necessarily allow for detailed objects to be distinguished through a thickness of 1 cm of the hair coloring composition. The term "transparent," however, refers to the characteristic of a composition to permit the passage of light and also allow for objects to be distinguished through a thickness of 1 cm of the hair coloring composition. Although microemulsions of the hair coloring composition may be translucent or transparent, the hair coloring compositions may optionally include colorants that provide a color to the hair coloring composition while also being translucent or transparent.

In some cases, the hair coloring compositions include less than 5 wt. %, preferably less than 3 wt. %, or preferably less than 1 wt. % of alkoxylated fatty alcohols. In some instances, the hair coloring compositions are free of or essentially free of alkoxylated fatty alcohols and, in particular, free of or essentially free of deceth-3. Additionally and/or alternatively, the hair coloring compositions may be formulated to include less than 6 wt. %, preferably less than 4 wt. %, preferably less than 2 wt. %, or preferably less than 1 wt. % of sulfate based anionic surfactants. In certain embodiments, the hair coloring compositions are free of or essentially free of sulfate based anionic surfactants.

Suitable components, such as those listed below, may be included or excluded from the formulations for the hair coloring compositions depending on the specific combination of other components, the form of the hair coloring compositions, and/or the use of the formulation (e.g., a lotion, a serum, gel, cream, etc.).

Oxidative Dyes

The hair coloring compositions include one or more oxidative dye precursors in an amount typically ranging from about 0.1 to about 10 by weight, based on the total weight of the hair coloring composition. For example, the total amount of oxidative dye precursors may be 0.1 wt. % or more, 0.2 wt. % or more, 0.3 wt. % or more, 0.4 wt. % or more, 0.5 wt. % or more, 0.6 wt. % or more, 0.7 wt. % or more, 0.8 wt. % or more, 0.9 wt. % or more, 1.0 wt. % or more and/or 20 wt. % or less, 15 wt. % or less, 13 wt. % or less, 11 wt. % or less, 10 wt. % or less, 9 wt. % or less, 8 wt. % or less, 7 wt. % or less, 6 wt. % or less, 5 wt. % or less, 4 wt. % or less, 3 wt. % or less, 2.5 wt. % or less, including ranges and sub-ranges therebetween, based on the total weight of the composition.

In some instances, the total amount of oxidative dye precursors may range from about 0.1 to about 10 wt. %, about 0.1 to about 9 wt. %, about 0.1 to about 8 wt. %, about 0.1 to about 7 wt. %, about 0.1 to about 6 wt. %, about 0.1 to about 5 wt. %, about 0.1 to about 4 wt. %, about 0.1 to about 3 wt. %, about 0.1 to about 2 wt. %, from about 0.5 to about 10 wt. %, about 0.5 to about 9 wt. %, about 0.5 to about 8 wt. %, about 0.5 to about 7 wt. %, about 0.5 to about 6 wt. %, about 0.5 to about 5 wt. %, about 0.5 to about 4 wt. %, about 0.5 to about 3 wt. %, or about 0.5 to about 2 wt. %, or from about 0.8 to about 10 wt. %, about 0.8 to about 9 wt. %, about 0.8 to about 8 wt. %, about 0.8 to about 7 wt. %, about 0.8 to about 6 wt. %, about 0.8 to about 5 wt. %, about 0.8 to about 4 wt. %, about 0.8 to about 3 wt. %, or about 0.8 to about 2 wt. %, including ranges and sub-ranges therebetween, based on the total weight of the composition.

An oxidative dye may be selected from any type of oxidative dye useful for imparting color to hair. The oxidative dye may also encompass a wide variety of oxidation dye precursors. These include primary dye intermediates and couplers.

Primary Dye Intermediates

Examples of primary dye intermediates include ortho or para aminophenols, ortho or para phenylenediamines, primary dye intermediates, double bases, heterocyclic bases, and the acid addition salts thereof. Para-phenylenediamines that may be suitably used with the hair coloring compositions disclosed herein include, but are not limited to, para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl) amino-2-methylaniline, 4-N,N-bis(β-hydroxyethyl)amino-2-chloroaniline, 2-(β-hydroxyethyl)-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-(β-hydroxyethyloxy)-para-phenylenediamine, 2-(β-acetylaminoethyloxy)-para-phenylenediamine, N-(β-methoxyethyl)-para-phenylenediamine, 2-methyl-1-N-(β-hydroxyethyl)-para-phenylenediamine and their addition salts with an acid. In some embodiments, the para-phenylenediamines include para-phenylenediamine, para-toluylenediamine, 2-isopropyl-para-phenylenediamine, 2-(β-hydroxyethyl)-para-phenylenediamine, 2-(β-hydroxyethyloxy)-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, hydroxypropyl bis(n-hydroxyethyl-p-phenylenediamine) hcl, 2-chloro-para-phenylenediamine and their addition salts with an acid.

The ortho-phenylenediamines include N1-(2-hydroxyethyl)-4-nitro-o-phenylenediamine, 4-methyl-o-phenylenediamine, and 4-nitro-o-phenylenediamine and acid addition salts thereof. As used herein, the term "double bases" means compounds comprising at least two aromatic nuclei having at least one of amino and hydroxyl groups. Examples include compounds corresponding to the following formula and their addition salts with an acid:

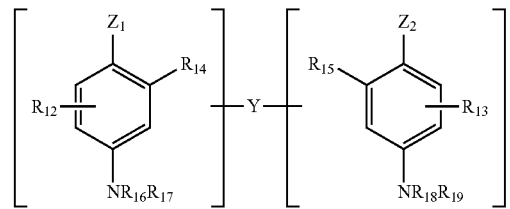

in which: $Z_1$ and $Z_2$, which are identical or different, represent a hydroxyl or —$NH_2$ radical that can be substituted by a $C_1$-$C_4$ alkyl radical or by a connecting arm Y. The connecting arm Y represents a linear or branched alkylene chain comprising from 1 to 14 carbon atoms which can be interrupted or terminated by one or more nitrogenous groups and/or by one or more heteroatoms, such as oxygen, sulphur or nitrogen atoms, and which is optionally substituted by one or more hydroxyl or $C_1$-$C_6$ alkoxy radicals. $R_{12}$ and $R_{13}$ represent a hydrogen or halogen atom, a $C_1$-$C_4$ alkyl radical, a $C_1$-$C_4$ monohydroxyalkyl radical, a $C_2$-$C_4$ polyhydroxyalkyl radical, a $C_1$-$C_4$ aminoalkyl radical or a connecting arm Y. $R_{14}$, $R_{15}$, $R_{16}$, $R_{17}$, $R_{18}$ and $R_{19}$, which are identical or different, represent a hydrogen atom, a connecting arm Y or a $C_1$-$C_4$ alkyl radical. It should be understood that the compounds of the above formula only comprise a single connecting arm Y per molecule. The nitrogenous groups of the above formula may be amino, mono($C_1$-$C_4$)alkylamino, di($C_1$-$C_4$)alkylamino, tri($C_1$-$C_4$)alkylamino, monohydroxy ($C_1$-$C_4$)alkylamino, imidazolinium and ammonium radicals. For example, the ortho-aminophenols that may be 2-aminophenol, 2-amino-5-methylphenol, 2-amino-6-methylphenol and 5-acetamido-2-aminophenol, and the addition salts thereof.

Additional examples of double bases of include of N,N'-bis(β-hydroxyethyl)-N,N'-bis(4'-aminophenyl)-1,3-di-amino-propanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-diethyl-N,N'-bis(4'-amino-3'-methylphenyl)ethylenediamine, 1,8-bis(2,5-diaminophenoxy)-3,5-dioxaoctane and their addition salts with an acid. In some instances, the double base is N,N'-Bis(β-hydroxyethyl)-N,N'-bis(4'-aminophenyl)-1,3-diaminopropanol, 1,8-bis(2,5-diaminophenoxy)-3,5-dioxaoctane or one of their addition salts with an acid.

Para-aminophenols that may be suitably employed include compounds having a structure in accordance with the following formula and their addition salts with an acid:

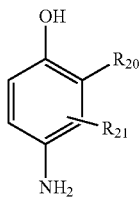

in which: $R_{20}$ represents a hydrogen atom, a halogen atom, such as fluorine, a $C_1$-$C_4$ alkyl radical, a $C_1$-$C_4$ monohydroxyalkyl radical, a $(C_1$-$C_4)$alkoxy$(C_1$-$C_4)$ alkyl radical, a $C_1$-$C_4$ aminoalkyl radical or a hydroxy$(C_1$-$C_4)$ alkylamino-$(C_1$-$C_4)$alkyl radical; and $R_{21}$ represents a hydrogen atom, a halogen atom, such as fluorine, a $C_1$-$C_4$ alkyl radical, a $C_1$-$C_4$ monohydroxyalkyl radical, a $C_2$-$C_4$ polyhydroxyalkyl radical, a $C_1$-$C_4$ aminoalkyl radical, a $C_1$-$C_4$ cyanoalkyl radical or a $(C_1$-$C_4)$alkoxy$(C_1$-$C_4)$alkyl radical. Additionally and/or alternatively, the para-aminophenols may be chosen from para-aminophenol, 4-amino-3-methylphenol, 4-amino-3-fluorophenol, 4-amino-3-hydroxymethylphenol, 4-amino-2-methylphenol, 4-amino-2-hydroxymethyl phenol, 4-amino-2-methoxymethylphenol, 4-amino-2-aminomethylphenol, 4-amino-2-(β-hydroxyethylaminomethyl)phenol, N-methyl-para-aminophenol, and the acid addition salts thereof.

The ortho-aminophenols that may be used as oxidation bases in the context of certain embodiments may be chosen from 2-aminophenol, 2-amino-1-hydroxy-5-methylbenzene, 2-amino-1-hydroxy-6-methylbenzene, 5-acetamido-2-aminophenol, and the acid addition salts thereof. Heterocyclic bases that may be used in the hair coloring composition include, e.g., pyridine derivatives, pyrimidine derivatives, pyrazole derivatives, pyrazolinone derivatives, and the acid addition salts thereof.

Pyridine derivatives that may be used in the hair coloring compositions include the compounds described, e.g., in patents GB 1,026,978 and GB 1,153,196, as well as the compounds 2,5-diaminopyridine, 2-(4-methoxyphenyl) amino-3-aminopyridine, 2,3-diamino-6-methoxypyridine, 2-(β-methoxyethyl)amino-3-amino-6 methoxypyridine, 3,4-diaminopyridine, and the acid salts thereof. Similarly, pyrimidine derivatives that may be used in the hair coloring compositions include the compounds disclosed, for example, in German Patent DE 2 359 399 or Japanese Patents JP 88-169 571 and JP 91-10659 or Patent Application WO 96/15765, such as 2,4,5,6-tetra-aminopyrimidine, 4-hydroxy-2,5,6-triaminopyrimidine, 2-hydroxy-4,5,6-triamino-pyrimidine, 2,4-dihydroxy-5,6-diaminopyrimidine, 2,5,6-triaminopyrimidine, and the pyrazolopyrimidine derivatives, such as those mentioned in French Application FR-A-2 750 048 and among which may be mentioned pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl)(2-hydroxyethyl)amino]ethanol; 2-[(7-amino-pyrazolo[1,5-a]pyrimidin-3-yl)(2-hydroxyethyl) amino]ethanol; 5,6-dimethyl-pyrazolo[1,5-a]pyrimidine-3, 7-diamine; 2,6-dimethylpyrazolo[1,5-a]pyrimidine-3,7-diamine; 2,5,N7,N7-tetramethylpyrazolo[1,5-a]pyrimidine-3,7-diamine; 3-amino-5-methyl-7-(imidazolylpropylamino) pyrazolo[1,5-a]pyrimidine; and their addition salts and their tautomeric forms, when there exists a tautomeric equilibrium, and their addition salts with an acid.

Pyrazole and pyrazolinone derivatives that may be employed in the hair coloring compositions include or be chosen from the compounds described in patents DE 3,843, 892, DE 4,133,957 and patent applications WO 94/08969, WO 94/08970, FR-A-2,733,749, and DE 19543988, such as 4,5-diamino-1-methyl-pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1, 3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-(β-hydroxyethyl)pyrazole, 4,5-diamino-1-ethyl-3-methylpyrazole, 4,5-diamino-1-ethyl-3-(4'-methoxyphenyl) pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl) amino-1,3-dimethyl-pyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl) amino-1-methylpyrazole, 2-(4,5-diamino-1H-pyrazol-1-yl), $H_2SO_4$, 2,3-diamino-6,7-dihydro-1H,5H-pyrazolo[1,2-z] pyrazol-1-one, 1-methyl-3-phenyl-2-pyrazolinone, and the acid addition salts thereof.

In some instances, primary intermediates that may be employed in the hair coloring compositions include p-phenylenediamine, p-aminophenol, o-aminophenol, N,N-bis(β-hydroxyethyl)-p-phenylenediamine, 2,5-diaminotoluene, their salts and mixtures thereof.

Additionally and/or alternatively, the oxidation bases may be selected from selected from 3-aminopyrazolo-[1,5-a]-pyridines and preferably substituted on carbon atom 2 by:
(a) one (di)($C_1$-$C_6$)(alkyl)amino group wherein said alkyl group can be substituted by at least one hydroxy, amino, imidazolium group;
(b) one heterocycloalkyl group containing from 5 to 7 members chain, and from 1 to 3 heteroatoms, potentially cationic, potentially substituted by one or more ($C_1$-$C_6$-alkyl, such as di($C_1$-$C_4$)alkylpiperazinium; or
(c) one ($C_1$-$C_6$)alkoxy potentially substituted by one or more hydroxy groups such as .quadrature.-hydroxyalkoxy, and the addition salts thereof.

Among the pyrimidine derivatives that may be mentioned are compounds such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Among the pyrazole derivatives that may be mentioned are compounds such as 4,5-diamino-1-methyl-pyrazole, 4,5-diamino-1-(.beta.-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenyl-pyrazole, 4,5-diamino-1-methyl-3-phenylpyrazole, 4-amino-1,3-dimethyl-5-hydrazinopyrazole, 1-benzyl-4,5-diamino-3-methyl-pyrazole, 4,5-diamino-3-tert-butyl-1-methylpyrazole, 4,5-diamino-1-tert-butyl-3-methylpyrazole, 4,5-diamino-1-(.beta.-hydroxyethyl)-3-methylpyrazole, 4,5-diamino-1-ethyl-3-methyl-pyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(.beta.-hydroxyethyl)amino-1-methylpyrazole, and the addition salts thereof. 4,5-Diamino-1-(.beta.-methoxyethyl)pyrazole may also be used.

Pyrazole derivatives that may also be mentioned include diamino-N,N-dihydropyrazolopyrazolones such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one. 2,3-Diamino-6,7-dihydro-1H,5H-pyrazolo[1,2-a]pyrazol-1-one and/or a salt thereof will preferably be used. 4,5-Diamino-1-(.beta.-hydroxyethyl)pyrazole and/or 2,3-diamino-6,7-dihydro-1H,5H-pyrazolo[1,2-a]pyrazol-1-one and/or a salt thereof will preferentially be used as heterocyclic bases.

Color Couplers

The hair coloring compositions may also contain coupler compounds. Suitable couplers that may be used include or may be chosen from meta-aminophenols, meta-phenylenediamines and meta-diphenols, naphthols, mono- or polyhydroxylated naphthalene derivatives, and heterocyclic couplers such as, for example, indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles, quinolines, benzomorpholine derivatives, pyrazoloazole derivatives, pyrroloazole derivatives, imidazoloazole derivatives, pyrazolopyrimidine derivatives, pyrazoline-3,5-dione derivatives, pyrrolo[3,2-d]oxazole derivatives, pyrazolo[3,4-d]thiazole derivatives, thiazoloazole S-oxide derivatives, thiazoloazole S,S-dioxide derivatives, and the acid addition salts thereof. In some embodiments, the color couplers include a structure in accordance with the following general formula:

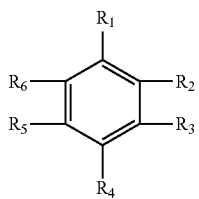

wherein $R_1$ is unsubstituted hydroxy or amino, or hydroxy or amino substituted with one or more $C_{1-6}$ hydroxyalkyl groups, $R_3$ and $R_5$ are each independently hydrogen, hydroxy, amino, or amino substituted with $C_{1-6}$ alkyl, $C_{1-6}$ alkoxy, or $C_{1-6}$ hydroxyalkyl group; and $R_2$, $R_4$, and $R_6$ are each independently hydrogen, $C_{1-6}$ alkoxy, $C_{1-6}$ hydroxyalkyl, or $C_{1-6}$ alkyl, or $R_3$ and $R_4$ together may form a methylenedioxy or ethylenedioxy group. Examples of such compounds include meta-derivatives such as phenols, meta-aminophenols, meta-phenylenediamines, and the like, which may be unsubstituted, or substituted on the amino group or benzene ring with alkyl, hydroxyalkyl, alkylamino groups, and the like. Suitable couplers include m-aminophenol, 2,4-diaminotoluene, 4-amino, 2-hydroxytoluene, phenyl methyl pyrazolone, 3,4-methylenedioxyphenol, 3,4-methylenedioxy-1-[(beta-hydroxyethyl)amino]benzene, 1-methoxy-2-amino-4-[(beta-hydroxyethyl)amino]benzene, 1-hydroxy-3-(dimethylamino)benzene, 6-methyl-1-hydroxy-3[(beta-hydroxyethyl)amino]benzene, 2,4-dichloro-1-hydroxy-3-aminobenzene, 1-hydroxy-3-(diethylamino) benzene, 1-hydroxy-2-methyl-3-aminobenzene, 2-chloro-6-methyl-1-hydroxy-3-aminobenzene, 1,3-diaminobenzene, 6-methoxy-1,3-diaminobenzene, 6-hydroxyethoxy-1,3-diaminobenzene, 6-methoxy-5-ethyl-1,3-diaminobenzene, 6-ethoxy-1,3-diaminobenzene, 1-bis(beta-hydroxyethyl)amino-3-aminobenzene, 2-methyl-1,3-diaminobenzene, 6-methoxy-1-amino-3-[(beta-hydroxyethyl)amino]-benzene, 6-(beta-aminoethoxy)-1,3-diaminobenzene, 6-(beta-hydroxyethoxy)-1-amino-3-(methylamino)benzene, 6-carboxymethoxy-1,3-diaminobenzene, 6-ethoxy-1-bis(beta-hydroxyethyl)amino-3-aminobenzene, 6-hydroxyethyl-1,3-diaminobenzene, 1-hydroxy-2-isopropyl-5-methylbenzene, 1,3-dihydroxybenzene, 2-chloro-1,3-dihydroxybenzene, 2-methyl-1,3-dihydroxybenzene, 4-chloro-1,3-dihydroxybenzene, 5,6-dichloro-2-methyl-1,3-dihydroxybenzene, 1-hydroxy-3-amino-benzene, 1-hydroxy-3-(carbamoylmethylamino)benzene, 6-hydroxybenzomorpholine, 4-methyl-2,6-dihydroxypyridine, 2,6-dihydroxypyridine, 2,6-diaminopyridine, 6-aminobenzomorpholine, 1-phenyl-3-methyl-5-pyrazolone, 1-hydroxynaphthalene, 1,7-dihydroxynaphthalene, 1,5-dihydroxynaphthalene, 5-amino-2-methyl phenol, 4-hydroxyindole, 4-hydroxyindoline, 6-hydroxyindole, 6-hydroxyindoline, 2,4-diaminophenoxyethanol, and mixtures thereof.

Other couplers that may be used include or be chosen from 2,4-diamino-1-(β-hydroxyethyloxy)benzene, 2-methyl-5-aminophenol, 5-N-(β-hydroxyethyl) amino-2-methylphenol, 3-aminophenol, 1,3-dihydroxybenzene, 1,3-dihydroxy-2-methylbenzene, 4-chloro-1,3-dihydroxybenzene, 2,4-diamino 1-(β-hydroxyethyloxy) benzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6-dimethylpyrazolo[3,2-c]-1,2,4-triazole, 2,6-dimethylpyrazolo[1,5-b]-1,2,4-triazole, 6-methyl pyrazolo[1,5-a]-benzimidazole, and the acid addition salts thereof. In some embodiments, the couplers include resorcinol, 1-naphthol, 2-methylresorcinol, 4-amino-2-hydroxy toluene, m-aminophenol, 2,4-diaminophenoxyethanol, phenyl methyl pyrazolone, hydroxybenzomorpholine, 2-methyl-5-hydroxyethylaminophenol, 6-hydroxyindole, 2-amino-3-hydroxypyridine, 5-amino-6-chloro-o-cresol, 4-chlororesorcinol, their salts, and mixtures thereof.

When they are present, couplers may be present in amounts ranging from 0.0001 to 12 wt. %; or from 0.001 to 8 wt. %, based on the total weight of the hair coloring composition. In general, the acid addition salts of the oxidation bases and couplers may be chosen from hydrochlorides, hydrobromides, sulphates, tartrates, lactates, and acetates.

Oxidizing Agent

The hair coloring compositions may require an oxidizing agent when the colorant comprises an oxidative dye. Oxidizing agents are used in an amount sufficient for the oxidative dye to develop a color. The oxidizing agents may be, e.g., peroxide, a persulfate, a perborate, a percarbonate, alkali metal bromates, ferricyanides, or a mixture thereof. Oxidizing agents that may also be used include at least one redox enzyme such as laccases, peroxidases, and 2-electron oxidoreductases, such as uricase, where appropriate in the presence of their respective donor or co-factor.

The oxidizing agent, e.g. hydrogen peroxide, may be present in an aqueous solution whose titre may range from 1 to 40 volumes, such as from 5 to 40 volumes. In certain embodiments, the oxidizing agent is a persulfate and/or a monopersulfate such as, e.g., potassium persulfate, sodium persulfate, ammonium persulfate, as well as mixtures thereof. In another embodiment, the oxidizing agents include at least one of or are chosen from hydrogen peroxide, potassium persulfate, sodium persulfate and mixtures thereof.

In general, the oxidizing agent may be present in an amount of at least 1% by weight, based on the total weight of the coloring composition. In certain embodiments, the oxidizing agent is present in an amount ranging from 1% by weight to 80% by weight, or from 5% by weight to 75% by weight, based on the total weight of the developer composition.

Typically, the oxidizing agent is provided in the form of a developer composition. The developer composition may be in the form of a powder, gel, liquid, foam, lotion, cream, mousse, and emulsion. In certain embodiments, the developer compositions may be aqueous or is in the form of an emulsion. In another embodiment, however, the developer composition is substantially anhydrous. The term "substantially anhydrous" means that the developer is either completely free of water or contains no appreciable amount of water, e.g., no more than 1% by weight or no more than 0.5% by weight, based on the weight of the developer composition. The developer composition can contain at least one solvent, chosen from water, organic solvents, and mixtures thereof.

When the developer composition is substantially anhydrous, developer composition may comprise at least one solvent chosen from organic solvents. Suitable organic solvents may, for some embodiments, include ethanol, isopropyl alcohol, benzyl alcohol, phenyl ethyl alcohol, glycols and glycol ethers, such as propylene glycol, hexylene glycol, ethylene glycol monomethyl, monoethyl or monobutyl ether, propylene glycol and its ethers, such as propylene glycol monomethyl ether, butylene glycol, dipropylene glycol, diethylene glycol alkyl ethers, such as diethylene glycol monoethyl ether and monobutyl ether, hydrocarbons such as straight chain hydrocarbons, mineral oil, polybutene, hydrogenated polyisobutene, hydrogenated polydecene, polydecene, squalane, petrolatum, isoparaffins, and mixtures thereof. The solvent may be present in an amount ranging, e.g., from 0.5% to 70% by weight, from 2% to 60% by weight, or from 5 to 50% by weight, relative to the total weight of the developer composition.

The pH of the developer composition can range from 2 to 12, such as from 6 to 11, and it may be adjusted to the desired value using basifying/alkalizing agents that are well known in the art of dyeing hair.

Non-Oxidative Dye Colorants

In addition to the oxidative dyes, the hair coloring composition may include one or more or additional non-oxidative dye colorants. The non-oxidative dye colorants can be any colorants appropriate for use on hair that is not an oxidative dye as discussed herein. For example, the colorant may be selected from direct dyes, pigments, natural colorants, and mixtures thereof. Other suitable hair colorants include, but are not limited to, liposoluble dyes, nacreous pigments, pearling agents, leuco dyes, optical lightening colorants, and optically-variable pigments. In some embodiments, the colorant includes at least one primary dye intermediate and/or a coupler compound.

Direct Dyes

A direct dye is a colored substance that does not require the use of an oxidizing agent in order to reveal its color. Suitable direct dyes that may be used in the hair coloring compositions may include or be chosen from acidic (anionic), basic (cationic), and neutral dyes. "Acidic dye" is generally intended to mean a dye containing at least one COOH, $SO_3H$, $PO_3H$, or $PO_4H_2$ group, it being possible for said groups to exist in the form of salts. "Salts" is generally intended to mean salts of metals (for example, alkali metals or alkaline earth metals), salts of an organic amine that may optionally be hydroxylated. Such dyes are also referred to as anionic dyes. Exemplary acidic dyes that may be suitably used in the hair coloring compositions include or can be chosen from acidic nitro dyes, acidic azo dyes, acidic azine dyes, acidic triarylmethane dyes, acidic quinone dyes, acidic indo-amine dyes and acidic natural dyes, and mixtures thereof.

"Basic dyes" is generally intended to mean a dye that has at least one group bearing a positive charge, such as an ammonium group or a quaternized nitrogen atom in a ring. Such dyes are also referred to as cationic dyes. Suitable basic dyes that may be used in hair coloring compositions include and/or can be chosen from nitrobenzene dyes, azo dyes, azomethine dyes, methine dyes, tetraazapentamethine dyes, anthraquinone dyes, naphthoquinone dyes, benzoquinone dyes, phenothiazine dyes, indigoid dyes, xanthene dyes, phenanthridine dyes, phthalocyanin dyes, triarylamethane-derived dyes and basic natural dyes, and mixtures thereof.

Preferably, the direct dyes may be present in amounts ranging from 0.001% to 30% by weight, preferably from 0.01% to 20% by weight, or more preferably from 0.1% to 10% by weight, based on the total weight of the coloring composition.

Pigments

The hair coloring compositions, in some instances, may include pigments, such as those chosen from white, colored, inorganic, organic, polymeric, nonpolymeric, coated and uncoated pigments. Non-limiting examples of mineral pigments include titanium dioxide, optionally surface-treated, zirconium oxide, zinc oxide, cerium oxide, iron oxides, chromium oxides, manganese violet, ultramarine blue, chromium hydrate, silica, ferric blue, and mixtures thereof. Non-limiting examples of organic pigments include carbon black, pigments of D & C type, and lakes based on cochineal carmine, barium, strontium, calcium, and aluminum. Other examples of pigments include ultramarines, HC Blue No. 14, Ext. Yellow 7, Yellow 10 Lake, and acid violet 43.

If present, the pigments may be present in the hair coloring composition in a concentration ranging up to 50 wt. % of the total weight of the coloring composition, such as from 0.5 to 40 wt. % or from 2 to 30 wt. % based on the total weight of the coloring composition.

Natural Colorants

The hair coloring composition may include one or more natural colorants. Non-limiting examples of natural colorants include those disclosed in US patent application publication no. US 2003/0159221, the entire contents of which is hereby incorporated by reference. As used herein, the phrase "natural colorant" refers to compounds that exist in nature, whether they have been obtained by extraction or reproduced chemically. Examples of natural direct dyes that may be used in the hair coloring composition include and/or may be chosen from lawsone, juglone, alizarin, purpurin, carminic acid, kermesic acid, purpurogallin, protocatechaldehyde, indigo, isatin, curcumin, spinulosin and apigenidin. It is also possible to use extracts or decoctions containing these natural dyes and especially henna-based poultices or extracts.

If present, the natural colorants may be incorporated in the hair coloring composition in a concentration ranging up to 50 wt. % based on the total weight of the hair coloring composition, such as from 0.05 to 40 wt. % or from 2 to 30 wt. % based on the total weight of the hair coloring composition.

Liposoluble Dyes

Optionally, the hair coloring composition may include one or more liposoluble dyes. Examples of liposoluble dyes that may be used in the hair coloring compositions include and/or may be chosen from Sudan Red, DC Red 17, DC Green 6, ß-carotene, soybean oil, Sudan Brown, DC Yellow 11, DC Violet 2, DC Orange 5, DC Blue No. 14, annatto, and quinoline yellow. The liposoluble dyes, when present, may have a concentration ranging up to 20 wt. % of the total weight of the hair coloring composition, such as from 0.0001 to 6 wt. % or 0.1 to 4 wt. % of the total weight of the hair coloring composition.

Nacreous Pigments

In some instances, the hair coloring composition includes one or more nacreous pigments. Exemplary nacreous pigments that may be used in the hair coloring compositions include and/or may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, may be present in the color base composition in a concentration ranging up to 50% by weight of the total weight of the hair coloring composition, such as from 0.1% to 20% or preferably from 0.1% to 15% by weight of the total weight of the hair coloring composition.

Leuco Dyes

The hair coloring compositions may also include one or more Leuco dyes. Non-limiting examples of leuco dyes include those disclosed in US patent application publication no. 20040194231, the entire content of which is hereby incorporated by reference. Leuco dyes are usually only slightly colored or are not colored at all and can be converted by simple oxidation in air or in the presence of an oxidizing agent into a triheteroylmethane compound. Examples of leuco dyes and corresponding triheteroylmethane compounds that may be used in the hair coloring compositions include and/or may be chosen from 1H-Benzo[ij]quinolizinium, 9-[bis(2,3,6,7-tetrahydro-1H,5H-benzo[ij-]quinolizin-9-yl)methylene]-2,3,5,6,7,9-hexahydro-chloride; 5H-Benzo[a]carbazolium, 11-ethyl-5-[(11-ethyl-11H-benzo[a]carbazol-5-yl)(1-ethyl-1,2,3,4-tetrahydro-5-quinolinyl)methylene]-; Pyrrolo[3,2,1-ij]quinolinium, 8-[bis(1,2,5,6-tetrahydro-4H-pyrrolo[-3,2,1-ij]quinolin-8-yl)methylene]-1,2,4,5,6,8-hexahydro-; Tri(9-ethy-9H-carbazol-3-yl) methane; bis(6-Chloro-9-ethy-9H-carbazol-3-yl)-(9-ethy-9H-carbazol-3-yl)methane; bis(1-(4-sulfo-butyl)-2,3,4,6-tetrahydro-quinolinium)-pyrid-4-yl-methane; bis(1-ethyl-2-methyl-1H-indol-3-yl)-(9-ethy-9H-carbazol-3-yl)methane; Tri(7-ethyl-7H-benzo[c]carbazol-10-yl)methane; bis((6-dimethylamino-3-methyl-1H-indol-2-yl)-2-furylmethane; bis ((6-dimethylamino-3-methyl-1H-indol-2-yl)-(pyrid-4-yl) methane; bis(1-ethyl-2-methyl-1H-indol-3-yl)-2-thienylmethane; 3-[(1-ethyl-2-methyl-1H-indol-3-yl)-(9-ethy-9H-carbazol-3-yl) methylene]-1-ethyl-2-methyl-3H-indolium; 3-[(1-ethyl-2-methyl-1H-indol-3-yl)-2-thienyl) methylene]-1-ethyl-2-methyl-3H-indolium; and combinations thereof.

Optical Lightening Colorants

Examples of optical lightening colorants include those disclosed in US patent application publication no. US20040205905, the entire content of which is hereby incorporated by reference.

Anionic Surfactant(s)

The hair coloring composition includes one or more anionic surfactants chosen from acyl amino acid surfactants. The amount of acyl amino acid surfactants in the hair coloring composition typically ranges from about 0.1 to about 15 wt. % of the total weight of the hair coloring composition.

In some instances, the total amount of anionic surfactants chosen from acyl amino acid surfactants may range from about 0.1 to about 20 wt. %, about 0.1 to about 15 wt. %, about 0.1 to about 10 wt. %, about 0.1 to about 8 wt. %, about 0.1 to about 6 wt. %, from about 0.5 to about 25 wt. % about 0.5 to about 20 wt. %, about 0.5 to about 15 wt. %, about 0.5 to about 10 wt. %, about 0.5 to about 8 wt. %, about 0.5 to 6 wt. %, from about 1 to about 25 wt. %, about 1 to about 20 wt. %, about 1 to about 15 wt. %, about 1 to about 10 wt. %, about 1 to about 8 wt. %, about 1 to about 6 wt. %, from about 1.5 to about 25 wt. %, about 1.5 to about 20 wt. %, about 1.5 to about 15 wt. %, about 1.5 to about 10 wt. %, about 1.5 to about 8 wt. %, or about 1.5 to about 6 wt. %, including ranges and sub-ranges therebetween, based on the total weight of the hair coloring composition.

The one or more acyl amino acid surfactants of the anionic surfactants may be chosen from acyl sarcosinates, acyl tau rates, acyl glycinates, acyl glutamates, salts thereof, and a mixture thereof. Preferably, the acyl amino acid surfactants are chosen from acyl glycinates. For example, the acyl glycinates may include or be chosen from sodium cocoyl glycinate, sodium lauroyl glycinate, sodium myristoyl glycinate, potassium lauroyl glycinate, potassium cocoyl glycinate, and a mixture thereof. In certain embodiments, the anionic surfactants chosen from acyl sarcosinates include or comprise sodium cocoyl glycinate.

Additionally and/or alternatively, the hair coloring compositions may be formulated to include less than 6 wt. %, preferably less than 4 wt. %, preferably less than 2 wt. %, or preferably less than 1 wt. % of sulfate based anionic surfactants. In certain embodiments, the hair coloring compositions are free of or essentially free of sulfate based anionic surfactants.

Examples of anionic surfactants that may, in some instances, incorporated into the hair coloring composition include those chosen from acyl isethionates, acyl amino acids (such as acyl taurates, acyl glycinates, acyl glutamates, and acyl sarcosinates), alkyl sulfonates, alkyl sulfosuccinates, alkyl sulfoacetates, alkoxylated monoacids, salts thereof, and a mixture thereof.

Acyl Isethionates

Non-limiting examples of acyl isethionates include those having a structure in accordance with the first and/or second formulas provided below:

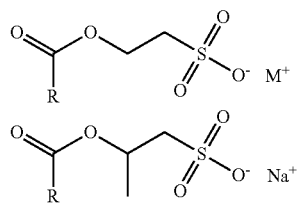

wherein R, $R^1$, $R^2$ and $R^3$ are each independently selected from H or an alkyl chain having 1-24 carbon atoms, said chain being saturated or unsaturated, linear or branched, and X is $COO^-$ or $SO_3^-$. Although sodium is shown as the cation in the second formula provided above, the cation for both formulas may be an alkali metal ion, such as sodium or potassium, ammonium ions, or alkanolammonium ions such as monoethanolammonium or triethanolammonium ions. Non-limiting examples of acyl isethionates include sodium isethionate, sodium cocoyl isethionate, sodium lauroyl methyl isethionate, and sodium cocoyl methyl isethionate.

Non-limiting examples of acyl isethionates include sodium isethionate, sodium cocoyl isethionate, sodium lauroyl methyl isethionate, and sodium cocoyl methyl isethionate. In certain embodiments, the hair coloring composition includes at least one or more acyl isethionates as the predominant type of anionic surfactant. The total amount of acyl isethionates in the hair coloring composition, if present, may vary but is typically from about 0.01 to about 20 wt. %, based on the total weight of the hair coloring composition. In some instance, the total amount of acyl isethionate(s) in the hair coloring composition is from about 0.01 to about 15 wt. %, about 0.1 to about 20 wt. %, about 0.1 to about 15 wt. %, about 1 to about 20 wt. %, about 1 to about 15 wt. %, about 5 to about 20 wt. %, about 5 to about 20 wt. %, or about 5 to about 15 wt. %, including ranges and sub-ranges therebetween, based on the total weight of the cleansing composition.

Acyl Amino Acids

Non-limiting examples of acyl amino acids that may be used in the hair coloring composition include and/or may be chosen from amino acid surfactants based on alanine, arginine, aspartic acid, glutamic acid, glycine, isoleucine, leucine, lysine, phenylalanine, serine, tyrosine, valine, sarcosine, threonine, and taurine. The cation associated with the acyl amino acid can be sodium or potassium. Alternatively, the cation can be an organic salt such as triethanolamine (TEA) or a metal salt. Non-limiting examples of useful acyl amino acids include having a structuring in accordance with the following formula:

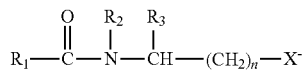

wherein R, $R^1$, $R^2$ and $R^3$ are each independently selected from H or an alkyl chain having 1-24 carbon atoms, said chain being saturated or unsaturated, linear or branched, and X is $COO^-$ or $SO_3^-$.

The total amount of acyl amino acids in the cleansing composition, if present, may vary but is typically from about 0.01 to about 15 wt. %, based on the total weight of the hair coloring composition. In some instance, the total amount of acyl amino acid(s) in the hair coloring composition is from about 0.01 to about 10 wt. %, about 0.01 to about 5 wt. %, about 0.1 to about 15 wt. %, about 0.1 to about 10 wt. %, about 0.1 to about 5 wt. %, about 1 to about 15 wt. %, about 1 to about 10 wt. %, or about 1 to about 5 wt. %, including ranges and sub-ranges therebetween, based on the total weight of the hair coloring composition.

Acyl Sarcosinates:

Non-limiting examples of acyl sarcosinates that may be used in the hair coloring composition include and/or can be chosen from potassium lauroyl sarcosinate, potassium cocoyl sarcosinate, sodium cocoyl sarcosinate, sodium lauroyl sarcosinate, sodium myristoyl sarcosinate, sodium oleoyl sarcosinate, sodium palmitoyl sarcosinate, and ammonium lauroyl sarcosinate. In some instances, sodium lauroyl sarcosinate is preferred. In some embodiments, more than one acyl sarcosinates are used in conjunction.

The total amount of acyl sarcosinates in the cleansing composition, if present, may vary but is typically from 0.01 to about 15 wt. %, based on the total weight of the cleansing composition. In some instance, the total amount of acyl amino acids in the cleansing composition is from about 0.01 to about 10 wt. %, about 0.01 to about 5 wt. %, about 0.1 to about 15 wt. %, about 0.1 to about 10 wt. %, about 0.1 to about 5 wt. %, about 1 to about 15 wt. %, about 1 to about 10 wt. %, or about 1 to about 5 wt. %, including ranges and sub-ranges therebetween, based on the total weight of the cleansing composition.

Acyl Taurates

Non-limiting examples of acyl taurates include those having a structure in accordance with the following formula:

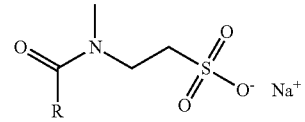

wherein R, $R^1$, $R^2$ and $R^3$ are each independently selected from H or an alkyl chain having 1-24 carbon atoms, or from 6-20 carbon atoms, or from 8 to 16 carbon atoms, said chain being saturated or unsaturated, linear or branched, and X is $COO^-$ or $SO_3^-$. Non-limiting examples of acyl taurate salts that may be used in the hair coloring composition include and/or may be chosen from sodium cocoyl taurate and sodium methyl cocoyl taurate.

The total amount of acyl taurate(s) in the hair coloring composition, if present, may vary but is typically from about 0.01 to about 15 wt. %, based on the total weight of the hair coloring composition. In some instance, the total amount of acyl taurates in the hair coloring composition is from about 0.01 to about 10 wt. %, about 0.01 to about 5 wt. %, about 0.1 to about 15 wt. %, about 0.1 to about 10 wt. %, about 0.1 to about 5 wt. %, about 1 to about 15 wt. %, about 1 to about 10 wt. %, or about 1 to about 5 wt. %, including ranges and sub-ranges therebetween, based on the total weight of the hair coloring composition.

Acyl Glycinates

Non-limiting examples of acyl glycinates that may be used in the hair coloring composition include those having a structure in accordance with the following formula:

wherein R is an alkyl chain of 8 to 16 carbon atoms. Although sodium is shown as the cation in the above formula, the cation may be an alkali metal ion such as sodium or potassium, ammonium ions, or alkanolammonium ions such as monoethanolammonium or triethanolammonium ions. Non-limiting examples of acyl glycinates that may be used in the hair coloring composition include and/or may be chosen from sodium cocoyl glycinate, sodium lauroyl glycinate, sodium myristoyl glycinate, potassium lauroyl glycinate, and potassium cocoyl glycinate, and in particular sodium cocoyl glycinate.

The total amount of acyl glycinates in the cleansing composition, if present, may vary but is typically from about 0.01 to about 15 wt. %, based on the total weight of the cleansing composition. In some instance, the total amount of acyl glycinates in the cleansing composition is from about 0.01 to about 10 wt. %, about 0.01 to about 5 wt. %, about 0.1 to about 15 wt. %, about 0.1 to about 10 wt. %, about 0.1 to about 5 wt. %, about 1 to about 15 wt. %, about 1 to about 10 wt. %, or about 1 to about 5 wt. %, including ranges and sub-ranges therebetween, based on the total weight of the cleansing composition.

Acyl Glutamates

Non-limiting examples that may be useful in the hair coloring compositions include those having a structuring in accordance with the following formula:

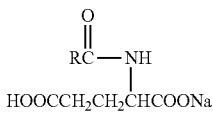

wherein R is an alkyl chain of 8 to 16 carbon atoms. Although sodium is shown as the cation in the above formula, the cation may be an alkali metal ion such as sodium or potassium, ammonium ions, or alkanolammonium ions such as monoethanolammonium or triethanolammonium ions. Non-limiting examples of acyl gluatamtes that may be used in the hair coloring composition include and/or may be chosen from dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, sodium undecylenoyl glutamate, triethanolamine mono-cocoyl glutamate, triethanolamine lauroylglutamate, and disodium cocoyl glutamate.

The total amount of acyl glutamates in the hair coloring composition, if present, may vary but is typically from about 0.01 to about 15 wt. %, based on the total weight of the hair coloring composition. In some instance, the total amount of acyl glutamates in the hair coloring composition is from about 0.01 to about 10 wt. %, about 0.01 to about 5 wt. %, about 0.1 to about 15 wt. %, about 0.1 to about 10 wt. %, about 0.1 to about 5 wt. %, about 1 to about 15 wt. %, about 1 to about 10 wt. %, or about 1 to about 5 wt. %, including ranges and sub-ranges therebetween, based on the total weight of the hair coloring composition.

Alkyl Sulfonates

Non-limiting examples of alkyl sulfonates that may be used in the hair coloring composition include and/or may be chosen from alkyl aryl sulfonates, primary alkane disulfonates, alkene sulfonates, hydroxyalkane sulfonates, alkyl glyceryl ether sulfonates, alpha-olefinsulfonates, sulfonates of alkylphenolpolyglycol ethers, alkylbenzenesulfonates, phenvlalkanesulfonates, alpha-olefinsulfonates, olefin sulfonates, alkene sulfonates, hydroxyalkanesulfonates and disulfonates, secondary alkanesulfonates, paraffin sulfonates, ester sulfonates, sulfonated fatty acid glycerol esters, and alpha-sulfo fatty acid methyl esters including methyl ester sulfonate.

In some embodiments, an alkyl sulfonate is used having a structure in accordance with the following formula:

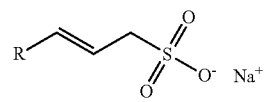

wherein R is selected from H or alkyl chain that has 1-24 carbon atoms, preferably 6-24 carbon atoms, more preferably, 8 to 20 carbon atoms, said chain being saturated or unsaturated, linear or branched. Although sodium is shown as the cation in the above formula, the cation may be an alkali metal ion such as sodium or potassium, ammonium ions, or alkanolammonium ions such as monoethanolammonium or triethanolammonium ions. In some instances, the alkyl sulfonate(s) include and/or are selected from $C_8$-$C_{16}$ alkyl benzene sulfonates, $C_{10}$-$C_{20}$ paraffin sulfonates, $C_{10}$-$C_{24}$ olefin sulfonates, salts thereof, and mixtures thereof. $C_{10}$-$C_{24}$ olefin sulfonates are particularly preferred.

The total amount of alkyl sulfonates in the hair coloring composition, if present, may vary but is typically from about 0.01 to about 15 wt. %, based on the total weight of the hair coloring composition. In some instance, the total amount of alkyl sulfonates in the hair coloring composition is from about 0.01 to about 10 wt. %, about 0.01 to about 5 wt. %, about 0.1 to about 15 wt. %, about 0.1 to about 10 wt. %, about 0.1 to about 5 wt. %, about 1 to about 15 wt. %, about 1 to about 10 wt. %, or about 1 to about 5 wt. %, including ranges and sub-ranges therebetween, based on the total weight of the hair coloring composition.

Alkyl Sulfosuccinates

Non-limiting examples of sulfosuccinates may include those having a structure in accordance with the following formula:

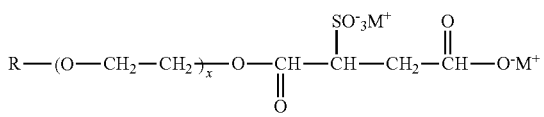

wherein R is a straight or branched chain alkyl or alkenyl group having 10 to 22 carbon atoms, preferably 10 to 20 carbon atoms, X is a number that represents the average degree of ethoxylation and can range from 0 to about 5, preferably from 0 to about 4, and most preferably from about 2 to about 3.5, and M and M' are monovalent cations which can be the same or different from each other. The cations may be alkali metal ions such as sodium or potassium, ammonium ions, or alkanolammonium ions such as monoethanolammonium or triethanolammonium ions.

Non-limiting examples of alkyl sulfosuccinates salts that may be used in the hair coloring composition include and/or may be chosen from disodium oleamido MIPA sulfosuccinate, disodium oleamido MEA sulfosuccinate, disodium lauryl sulfosuccinate, disodium laureth sulfosuccinate, diammonium lauryl sulfosuccinate, diammonium laureth sulfosuccinate, dioctyl sodium sulfosuccinate, disodium oleamide MEA sulfosuccinate, sodium dialkyl sulfosuccinate, and a mixture thereof.

The total amount of alkyl sulfosuccinates in the hair coloring composition, if present, may vary but is typically from about 0.01 to about 15 wt. %, based on the total weight of the hair coloring composition. In some instance, the total amount of alkyl sulfosuccinates in the hair coloring composition is from about 0.01 to about 10 wt. %, about 0.01 to about 5 wt. %, about 0.1 to about 15 wt. %, about 0.1 to about 10 wt. %, about 0.1 to about 5 wt. %, about 1 to about 15 wt. %, about 1 to about 10 wt. %, or about 1 to about 5 wt. %, including ranges and sub-ranges therebetween, based on the total weight of the hair coloring composition.

Alkyl Sulfoacetates

Non-limiting examples of alkyl sulfoacetates that may be used in the hair coloring composition include, e.g., alkyl sulfoacetates such as C4-C18 fatty alcohol sulfoacetates and/or salts thereof. A preferred sulfoacetate salt is sodium lauryl sulfoacetate. Useful cations for the salts may include alkali metal ions such as sodium or potassium, ammonium ions, or alkanolammonium ions such as monoethanolammonium or triethanolammonium ions.

The total amount of alkyl sulfoacetates in the hair coloring composition, if present, may vary but is typically from about 0.01 to about 15 wt. %, based on the total weight of the hair coloring composition. In some instance, the total amount of alkyl sulfoacetates in the hair coloring composition is from about 0.01 to about 10 wt. %, about 0.01 to about 5 wt. %, about 0.1 to about 15 wt. %, about 0.1 to about 10 wt. %, about 0.1 to about 5 wt. %, about 1 to about 15 wt. %, about 1 to about 10 wt. %, or about 1 to about 5 wt. %, including ranges and sub-ranges therebetween, based on the total weight of the hair coloring composition.

Alkoxylated Monoacids

Non-limiting examples of alkoxylated monoacids include compounds having a structure in accordance with the following formula:

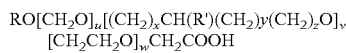

$$RO[CH_2O]_u[(CH_2)_xCH(R')(CH_2)_y(CH_2)_zO]_v[CH_2CH_2O]_wCH_2COOH$$

wherein:

R is a hydrocarbon radical containing from about 6 to about 40 carbon atoms;

u, v and w, independently of one another, represent numbers of from 0 to 60;

x, y and z, independently of one another, represent numbers of from 0 to 13;

R' represents hydrogen, alkyl, and the sum of x+y+z>0;

Compounds corresponding to the above formula can be obtained by alkoxylation of alcohols ROH with ethylene oxide as the sole alkoxide or with several alkoxides and subsequent oxidation. The numbers u, v, and w each represent the degree of alkoxylation. Whereas, on a molecular level, the numbers u, v and w and the total degree of alkoxylation can only be integers, including zero, on a macroscopic level they are mean values in the form of broken numbers.

Additionally, in the above formula, R may be linear or branched, acyclic or cyclic, saturated or unsaturated, aliphatic or aromatic, substituted or unsubstituted. Typically, R is a linear or branched, acyclic C6-40 alkyl or alkenyl group or a C1-40 alkyl phenyl group, more typically a C8-22 alkyl or alkenyl group or a C4-18 alkyl phenyl group, and even more typically a C12-18 alkyl group or alkenyl group or a C6-16 alkyl phenyl group; u, v, w, independently of one another, is typically a number from 2 to 20, more typically a number from 3 to 17 and most typically a number from 5 to 15; x, y, z, independently of one another, is typically a number from 2 to 13, more typically a number from 1 to 10 and most typically a number from 0 to 8.

Suitable alkoxylated monoacids that may be used in the hair coloring composition include and/or may be chosen from Butoxynol-5 Carboxylic Acid, Butoxynol-19 Carboxylic Acid, Capryleth-4 Carboxylic Acid, Capryleth-6 Carboxylic Acid, Capryleth-9 Carboxylic Acid, Ceteareth-25 Carboxylic Acid, Coceth-7 Carboxylic Acid, C9-11 Pareth-6 Carboxylic Acid, C11-15 Pareth-7 Carboxylic Acid, C12-13 Pareth-5 Carboxylic Acid, C12-13 Pareth-8 Carboxylic Acid, C12-13 Pareth-12 Carboxylic Acid, C12-15 Pareth-7 Carboxylic Acid, C12-15 Pareth-8 Carboxylic Acid, C14-15 Pareth-8 Carboxylic Acid, Deceth-7 Carboxylic Acid, Laureth-3 Carboxylic Acid, Laureth-4 Carboxylic Acid, Laureth-5 Carboxylic Acid, Laureth-6 Carboxylic Acid, Laureth-8 Carboxylic Acid, Laureth-10 Carboxylic Acid, Laureth-11 Carboxylic Acid, Laureth-12 Carboxylic Acid, Laureth-13 Carboxylic Acid, Laureth-14 Carboxylic Acid, Laureth-17 Carboxylic Acid, PPG-6-Laureth-6 Carboxylic Acid, PPG-8-Steareth-7 Carboxylic Acid, Myreth-3 Carboxylic Acid, Myreth-5 Carboxylic Acid, Nonoxynol-5 Carboxylic Acid, Nonoxynol-8 Carboxylic Acid, Nonoxynol-10 Carboxylic Acid, Octeth-3 Carboxylic Acid, Octoxynol-20 Carboxylic Acid, Oleth-3 Carboxylic Acid, Oleth-6 Carboxylic Acid, Oleth-10 Carboxylic Acid, PPG-3-Deceth-2 Carboxylic Acid, Capryleth-2 Carboxylic Acid, Ceteth-13 Carboxylic Acid, Deceth-2 Carboxylic Acid, Hexeth-4 Carboxylic Acid, Isosteareth-6 Carboxylic Acid, Isosteareth-11 Carboxylic Acid, Trudeceth-3 Carboxylic Acid, Trideceth-6 Carboxylic Acid, Trideceth-8 Carboxylic Acid, Trideceth-12 Carboxylic Acid, Trideceth-3 Carboxylic Acid, Trideceth-4 Carboxylic Acid, Trideceth-7 Carboxylic Acid, Trideceth-15 Carboxylic Acid, Trideceth-19 Carboxylic Acid, Undeceth-5 Carboxylic Acid and mixtures thereof. In certain embodiments, the ethoxylated acids are chosen from Oleth-10 Carboxylic Acid, Laureth-5 Carboxylic Acid, Laureth-11 Carboxylic Acid, and a mixture thereof.

The total amount of alkoxylated monoacids in the hair coloring composition, if present, may vary but is typically from about 0.01 to about 15 wt. %, based on the total weight of the cleansing composition. In some instance, the total amount of alkoxylated monoacids in the hair coloring composition is from about 0.01 to about 10 wt. %, about 0.01 to about 5 wt. %, about 0.1 to about 15 wt. %, about 0.1 to about 10 wt. %, about 0.1 to about 5 wt. %, about 1 to about 15 wt. %, about 1 to about 10 wt. %, or about 1 to about 5 wt. %, including ranges and sub-ranges therebetween, based on the total weight of the hair coloring composition.

Amphoteric Surfactant(s)

The hair coloring compositions include one or more amphoteric surfactants typically in the range of about 0.1 to about 15 wt. % of the total weight of the hair coloring composition. For example, the total amount of amphoteric surfactants may range from about 0.1 to about 25 wt. %, about 0.1 to about 20 wt. %, about 0.1 to about 15 wt. %, about 0.1 to about 10 wt. %, about 0.1 to about 8 wt. %, about 0.1 to about 6 wt. %; from about 0.5 to about 25 wt. % about 0.5 to about 20 wt. %, about 0.5 to about 15 wt. %, about 0.5 to about 10 wt. %, about 0.5 to about 8 wt. %, about 0.5 to 6 wt. %; from about 1 to about 25 wt. %, about 1 to about 20 wt. %, about 1 to about 15 wt. %, about 1 to about 10 wt. %, about 1 to about 8 wt. %, about 1 to about 6 wt. %; from about 1.5 to about 25 wt. %, about 1.5 to about 20 wt. %, about 1.5 to about 15 wt. %, about 1.5 to about 10 wt. %, about 1.5 to about 8 wt. %, about 1.5 to about 6 wt. %; from about 2 to about 25 wt. %, about 2 to about 20 wt. %, about 2 to about 15 wt. %, about 2 to about 10 wt. %, about 2 to about 8 wt. %, or about 2 to about 6 wt. %, including ranges and sub-ranges therebetween, based on the total weight of the hair coloring composition.

Amphoteric surfactants that may be useful in the hair coloring compositions disclosed herein may include or be chosen from betaines, sultaines, amphoacetates, amphoproprionates, and mixtures thereof. More typically, betaines and amphoproprionates are used, and most typically betaines. Betaines which can be used in the current compositions include those having the formulas below:

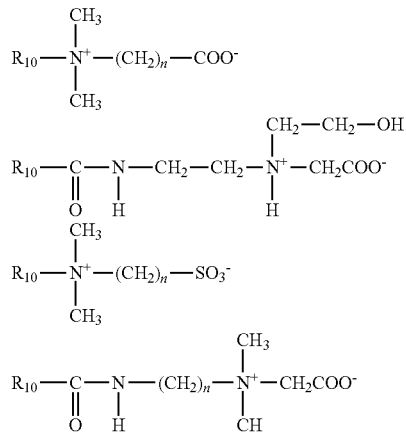

wherein $R^{10}$ is an alkyl group having 8-18 carbon atoms; and n is an integer from 1 to 3.

Particularly useful betaines may, in some instances, include coco betaine, cocoamidopropyl betaine, lauryl betaine, laurylhydroxy sulfobetaine, lauryldimethyl betaine, cocoamidopropyl hydroxysultaine, behenyl betaine, capryl/capramidopropyl betaine, lauryl hydroxysultaine, stearyl betaine, and mixtures thereof. For example, the betaine compound(s) may be selected from the group consisting of coco betaine, cocoamidopropyl betaine, behenyl betaine, capryl/capramidopropyl betaine, lauryl betaine, and mixtures thereof.

Non-limiting examples of hydroxyl sultaines include the following:

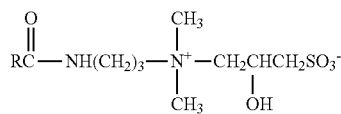

wherein

R is an alkyl group having 8-18 carbon atoms.

Non-limiting examples of alkylamphoacetates include those having the formula:

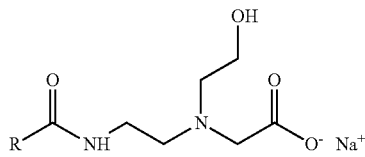

wherein R is an alkyl group having 8-18 carbon atoms.

Non-limiting examples of alkyl amphodiacetates include those having the formula:

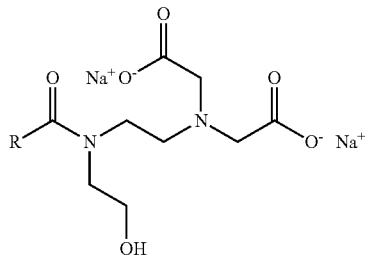

wherein R is an alkyl group having 8-18 carbon atoms.

The amphoteric surfactants of the present disclosure may be optionally quaternized secondary or tertiary aliphatic amine derivatives, in which the aliphatic group is a linear or branched chain comprising from 8 to 22 carbon atoms, said amine derivatives containing at least one anionic group, for instance a carboxylate, sulfonate, sulfate, phosphate or phosphonate group.

Preferably, the one or more amphoteric surfactants are chosen from betaines, alkyl sultaines, alkyl amphoacetates, alkyl amphoproprionates, salts thereof, and a mixture thereof. For example, the one or more amphoteric surfactants may include one or more betaines. Suitable betaines may, in some instances, be chosen from coco betaine, cocamidopropyl betaine, lauryl betaine, laurylhydroxy sulfobetaine, lauryldimethyl betaine, cocamidopropyl hydroxysultaine, behenyl betaine, capryl/capramidopropyl betaine, lauryl hydroxysultaine, stearyl betaine, and mixtures thereof. In certain embodiments, the one or more amphoteric surfactants are or include cocamidopropyl betaine.

Nonionic Surfactants

The hair coloring compositions include a plurality of nonionic surfactants. The plurality of nonionic surfactants are typically in an amount ranging from about 0.1 to about 30 wt. % of the total weight of the hair coloring composition.

For example, the total weight of the plurality of nonionic surfactants may range from about 0.1 to about 35 wt. %, about 0.1 to about 30 wt. %, about 0.1 to about 25 wt. %, about 0.1 to about 20 wt. %, about 0.1 to about 15 wt. %, about 0.1 to about 10 wt. %, about 0.1 to about 8 wt. %; from about 0.5 to about 35 wt. %, about 0.5 to about 30 wt. %, about 0.5 to about 25 wt. %, about 0.5 to about 20 wt. %, about 0.5 to about 15 wt. %, about 0.5 to about 10 wt. %, about 0.5 to about 8 wt. %; from about 1 to about 35 wt. %, about 1 to about 30 wt. %, about 1 to about 25 wt. %, about 1 to about 20 wt. %, about 1 to about 15 wt. %, about 1 to about 10 wt. %, about 1 to about 8 wt. %; from about 1.5 to about 35 wt. %, about 1.5 to about 30 wt. %, about 1.5 to about 25 wt. %, about 1.5 to about 20 wt. %, about 1.5 to about 15 wt. %, about 1.5 to about 10 wt. %, about 1.5 to about 8 wt. %; from about 2 to about 35 wt. %, about 2 to about 30 wt. %, about 2 to about 25 wt. %, about 2 to about 20 wt. %, about 2 to about 15 wt. %, about 2 to about 10 wt. %, about 2 to about 8 wt. %; from about 2.5 to about 35 wt. %, about 2.5 to about 30 wt. %, about 2.5 to about 25 wt. %, about 2.5 to about 20 wt. %, about 2.5 to about 15 wt. %, about 2.5 to about 10 wt. %, about 2.5 to about 8 wt. %; from about 3 to about 35 wt. %, about 3 to about 30 wt. %, about 3 to about 25 wt. %, about 3 to about 20 wt. %, about 3 to about 15 wt. %, about 3 to about 10 wt. %, about 3 to about 8 wt. %; from about 3.5 to about 35 wt. %, about 3.5 to about 30 wt. %, about 3.5 to about 25 wt. %, about 3.5 to about 20 wt. %, about 3.5 to about 15 wt. %, about 3.5 to about 10 wt. %, about 3.5 to about 8 wt. %, including ranges and sub-ranges therebetween, based on the total weight of the composition.

The plurality of the nonionic surfactants include, in some instances, less than than 5 wt. %, preferably less than 3 wt. %, preferably less than 1 wt. %, of alkoxylated fatty alcohol. In certain embodiments, the hair coloring composition is free of or essentially free of alkoxylated fatty alcohols. For example, the hair coloring composition may be free or essentially free of deceth-3 or similar compounds.

The plurality of nonionic surfactants includes at least one or more alkyl polyglucosides one or more sorbitan derivatives, and one or more polyol esters.

Alkyl Polyglucoside(s)

The plurality of nonionic surfactants includes one or more alkyl polyglucosides typically in an amount ranging from about 0.1 to about 15 wt. % of the total weight of the hair coloring composition. For example, the amount of alkyl polyglucosides may range from about 0.1 to about 25 wt. %, about 0.1 to about 20 wt. %, about 0.1 to about 15 wt. %, about 0.1 to about 10 wt. %, about 0.1 to about 8 wt. %, about 0.1 to about 6 wt. %; from about 0.5 to about 25 wt. % about 0.5 to about 20 wt. %, about 0.5 to about 15 wt. %, about 0.5 to about 10 wt. %, about 0.5 to about 8 wt. %, about 0.5 to 6 wt. %; from about 1 to about 25 wt. %, about 1 to about 20 wt. %, about 1 to about 15 wt. %, about 1 to about 10 wt. %, about 1 to about 8 wt. %, about 1 to about 6 wt. %; from about 1.5 to about 25 wt. %, about 1.5 to about 20 wt. %, about 1.5 to about 15 wt. %, about 1.5 to about 10 wt. %, about 1.5 to about 8 wt. %, about 1.5 to about 6 wt. %; from about 2 to about 25 wt. %, about 2 to about 20 wt. %, about 2 to about 15 wt. %, about 2 to about 10 wt. %, about 2 to about 8 wt. %, about 2 to about 6 wt. %; from about 2.5 to about 25 wt. %, about 2.5 to about 20 wt. %, about 2.5 to about 15 wt. %, about 2.5 to about 10 wt. %, about 2.5 to about 8 wt. %, about 2.5 to about 6 wt. %; from about 3 to about 25 wt. %, about 3 to about 20 wt. %, about 3 to about 15 wt. %, about 3 to about 10 wt. %, about 3 to about 8 wt. %, or about 3 to about 6 wt. %, including ranges and sub-ranges therebetween, based on the total weight of the hair coloring composition.

In some embodiments, the one or more alkyl polyglucosides include those chosen from lauryl glucoside, octyl glucoside, decyl glucoside, coco glucoside, caprylyl/capryl glucoside, sodium lauryl glucose carboxylate, and a mixture thereof. In some cases, the aplkyl polyglucosides includes or is chosen from lauryl glucoside. Additionally or alternatively, the alkyl polyglucosides may be chosen from glycerol $(C_6-C_{24})$alkylpolyglycosides including, e.g., polyethoxylated fatty acid mono or diesters of glycerol $(C_6-C_{24})$ alkylpolyglycosides. Additional alkyl polyglucosides that may be suitably incorporated, in some instances, in the hair coloring composition includes alkyl polyglucosides having a structure according to the following formula:

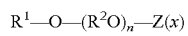

$R^1-O-(R^2O)_n-Z(x)$ wherein $R^1$ is an alkyl group having 8-18 carbon atoms; $R^2$ is an ethylene or propylene group; Z is a saccharide group with 5 to 6 carbon atoms; n is an integer from 0 to 10; and x is an integer from 1 to 5.

Useful alkyl poly glucosides may, in some instances, include lauryl glucoside, octyl glucoside, decyl glucoside, coco glucoside, caprylyl/capryl glucoside, and sodium lauryl glucose carboxylate. Typically, the at least one alkyl poly glucoside compound is selected from the group consisting of lauryl glucoside, decyl glucoside and coco glucoside. In some instances, decyl glucoside is particularly preferred.

Sorbitan Derivative(s)

The plurality of nonionic surfactants also includes one or more sorbitan derivatives typically in an amount ranging from about 0.1 to about 15 wt. % of the total weight of the hair coloring composition. For example, the total amount of sorbitan derivatives may range from about 0.1 to about 25 wt. %, about 0.1 to about 20 wt. %, about 0.1 to about 15 wt. %, about 0.1 to about 10 wt. %, about 0.1 to about 8 wt. %, about 0.1 to about 6 wt. %; from about 0.5 to about 25 wt. % about 0.5 to about 20 wt. %, about 0.5 to about 15 wt. %, about 0.5 to about 10 wt. %, about 0.5 to about 8 wt. %, about 0.5 to 6 wt. %; from about 1 to about 25 wt. %, about 1 to about 20 wt. %, about 1 to about 15 wt. %, about 1 to about 10 wt. %, about 1 to about 8 wt. %, about 1 to about 6 wt. %; from about 1.5 to about 25 wt. %, about 1.5 to about 20 wt. %, about 1.5 to about 15 wt. %, about 1.5 to about 10 wt. %, about 1.5 to about 8 wt. %, about 1.5 to about 6 wt. %; from about 2 to about 25 wt. %, about 2 to about 20 wt. %, about 2 to about 15 wt. %, about 2 to about 10 wt. %, about 2 to about 8 wt. %, about 2 to about 6 wt. %; from about 2.5 to about 25 wt. %, about 2.5 to about 20 wt. %, about 2.5 to about 15 wt. %, about 2.5 to about 10 wt. %, about 2.5 to about 8 wt. %, about 2.5 to about 6 wt. %; from about 3 to about 25 wt. %, about 3 to about 20 wt. %, about 3 to about 15 wt. %, about 3 to about 10 wt. %, about 3 to about 8 wt. %, or about 3 to about 6 wt. %, including ranges and sub-ranges therebetween, based on the total weight of the hair coloring composition.

Suitable sorbitan derivatives that may be incorporated into the plurality of nonionic surfactants include those chosen from polysorbate-20 (POE(20) sorbitan monolaurate), polysorbate-21 (POE(4) sorbitan monolaurate), polysorbate-40 (POE(20) sorbitan monopalmitate), polysorbate-60 (POE(20) sorbitan monostearate), polysorbate-61 (POE (4) sorbitan monostearate), polysorbate-65 (POE(20) sorbitan tristearate), polysorbate-80 (POE(20)sorbitan monooleate), polysorbate-81 (POE(4) sorbitan monooleate), polysorbate 85 (POE(20) Sorbitan Trioleate), sorbitan isostearate, sorbitan monolaurate, sorbitan monooleate, sorbitan monopalmitate, sorbitan monostearate, sorbitan sesquioleate, sorbitan trioleate and sorbitan tristearateand a mixture thereof.

Additional and/or alternative sorbitan derivatives include sorbitan esters including, e.g., esters of $C_{16}-C_{22}$ fatty acid and of sorbitan that were formed by esterification, with sorbitol, of at least one fatty acid comprising at least one saturated or unsaturated linear alkyl chain respectively having from 16 to 22 carbon atoms. These esters can be chosen in particular from sorbitan stearates, behenates, arachidates, palmitates or oleates, and their mixtures. Examples of optional sorbitan esters include sorbitan monostearate (CTFA name: Sorbitan stearate) sold by Croda under the name Span 60, the sorbitan tristearate sold by Croda under the name Span 65 V, the sorbitan monopalmitate (CTFA name: Sorbitan palmitate) sold by Croda under the name Span 40, the sorbitan monooleate sold by Croda under the name Span 80 V or the sorbitan trioleate sold by Uniqema under the name Span 85 V. Preferably, the sorbitan ester used is sorbitan tristearate.

Polyol Ester(s)

The plurality of nonionic surfactants further includes one or more polyol esters typically in an amount ranging from about 0.1 to about 15 wt. % of the total weight of the hair coloring composition. For example, the total amount of the one or more polyol esters may range from about 0.1 to about 20 wt. %, about 0.1 to about 15 wt. %, about 0.1 to about 10 wt. %, about 0.1 to about 8 wt. %, about 0.1 to about 6 wt. %; from about 0.5 to about 20 wt. %, about 0.5 to about 15 wt. %, about 0.5 to about 10 wt. %, about 0.5 to about 8 wt. %, about 0.5 to 6 wt. %; from about 0.8 to about 20 wt. %, about 0.8 to about 15 wt. %, about 0.8 to about 10 wt. %, about 0.8 to about 8 wt. %, about 0.8 to 6 wt. %; from about 1 to about 20 wt. %, about 1 to about 15 wt. %, about 1 to about 10 wt. %, about 1 to about 8 wt. %, about 1 to about 6 wt. %, including ranges and sub-ranges therebetween, based on the total weight of the hair coloring composition.

Non-limiting examples of the one or more polyol esters of the plurality of nonionic surfactants include those chosen from alkoxylated polyol esters. For instance, the alkoxylated polyol esters may be chosen from pegylated derivatives of propylene glycol oleate, propylene glycol caprylate/caprate, propylene glycol cocoate, propylene glycol stearate, and a mixture thereof. In certain embodiments, the alkoxylated polyol esters are chosen from PEG-55 propylene glycol oleate, PEG-6 propylene glycol caprylate/caprate, PEG-8 propylene glycol cocoate, PEG-25 propylene glycol stearate, and PEG-120 propylene glycol stearate, and a mixture thereof. In some instances, the polyol ester is or includes PEG-55 propylene glycol oleate. Additionally and/or alternatively, the polyol esters may be chosen from ethoxylated fatty acid esters of sorbitan comprising from 2 to 30 mol of ethylene oxide.

In some cases, the nonionic surfactant may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; and mixtures thereof.

Examples of ethoxylated fatty esters that may be mentioned include the adducts of ethylene oxide with esters of lauric acid, palmitic acid, stearic acid or behenic acid, and mixtures thereof, especially those containing from 9 to 100 oxyethylene groups, such as PEG-9 to PEG-50 laurate (as the CTFA names: PEG-9 laurate to PEG-50 laurate); PEG-9 to PEG-50 palmitate (as the CTFA names: PEG-9 palmitate to PEG-50 palmitate); PEG-9 to PEG-50 stearate (as the CTFA names: PEG-9 stearate to PEG-50 stearate); PEG-9 to PEG-50 palmitostearate; PEG-9 to PEG-50 behenate (as the CTFA names: PEG-9 behenate to PEG-50 behenate); polyethylene glycol 100 EO monostearate (CTFA name: PEG-100 stearate); and mixtures thereof.

Sources of unsaturated polyol esters of glycerol include synthesized oils, natural oils (e.g., vegetable oils, algae oils, bacterial derived oils, and animal fats), combinations of these, and the like. Non-limiting examples of vegetable oils include Abyssinian oil, Almond oil, Apricot oil, Apricot Kernel oil, Argan oil, Avocado oil, Babassu oil, Baobab oil, Black Cumin oil, Black Currant oil, Borage oil, Camelina oil, Carinata oil, Canola oil, Castor oil, Cherry Kernel oil, Coconut oil, Corn oil, Cottonseed oil, Echium oil, Evening Primrose oil, Flax Seed oil, Grape Seed oil, Grapefruit Seed oil, Hazelnut oil, Hemp Seed oil, Jatropha oil, Jojoba oil, Kukui Nut oil, Linseed oil, Macadamia Nut oil, Meadowfoam Seed oil, Moringa oil, Neem oil, Olive oil, Palm oil, Palm Kernel oil, Peach Kernel oil, Peanut oil, Pecan oil, Pennycress oil, Perilla Seed oil, Pistachio oil, Pomegranate Seed oil, Pongamia oil, Pumpkin Seed oil, Raspberry oil, Red Palm Olein, Rice Bran oil, Rosehip oil, Safflower oil, Seabuckthorn Fruit oil, Sesame Seed oil, Shea Olein, Sunflower oil, Soybean oil, Tonka Bean oil, Tung oil, Walnut oil, Wheat Germ oil, High Oleoyl Soybean oil, High Oleoyl Sunflower oil, High Oleoyl Safflower oil, High Erucic Acid Rapeseed oil, combinations of these, and the like. Non-limiting examples of animal fats include lard, tallow, chicken fat, yellow grease, fish oil, emu oil, combinations of these, and the like. Non-limiting example of a synthesized oil includes tall oil, which is a byproduct of wood pulp manufacture. In some embodiments, the natural oil is refined, bleached, and/or deodorized.

The polyol esters may optionally be a natural polyol esters chosen from vegetable oil, an animal fat, an algae oil and mixtures thereof; and said synthetic polyol ester is derived from a material selected from the group consisting of ethylene glycol, propylene glycol, glycerol, polyglycerol, polyethylene glycol, polypropylene glycol, poly(tetramethylene ether) glycol, pentaerythritol, dipentaerythritol, tripentaerythritol, trimethylolpropane, neopentyl glycol, a sugar, in one aspect, sucrose, and mixtures thereof.

Additional non-limiting examples of nonionic surfactants that may optionally be used in the hair coloring composition include and/or may be chosen from alkanolamides; polyoxyalkylenated nonionic surfactants; polyglycerolated nonionic surfactants; ethoxylated fatty esters; alcohols, alphadiols, alkylphenols and esters of fatty acids, being ethoxylated, propoxylated or glycerolated; copolymers of ethylene oxide and/or of propylene oxide; condensates of ethylene oxide and/or of propylene oxide with fatty alcohols; polyethoxylated fatty amides; ethoxylated oils from plant origin; fatty acid esters of sucrose; fatty acid esters of polyethylene glycol; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and mixtures thereof.

In some instances, the additional nonionic surfactants that may optionally be used in the hair coloring composition include and/or may be chosen from alkylphenols and esters of fatty acids, being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and mixtures thereof.

As glyceryl esters of fatty acids, glyceryl stearate (glyceryl mono-, di- and/or tristearate) (CTFA name: glyceryl stearate) or glyceryl ricinoleate and mixtures thereof can in particular be cited. As glyceryl esters of $C_8$-$C_{24}$ alkoxylated fatty acids, polyethoxylated glyceryl stearate (glyceryl mono-, di- and/or tristearate) such as PEG-20 glyceryl stearate can for example be cited.

Non-limiting examples alkanolamides include fatty acid alkanolamides. The fatty acid alkanolamides may be fatty acid monoalkanolamides or fatty acid dialkanolamides or fatty acid isoalkanolamides, and may have a $C_{2-8}$ hydroxyalkyl group (the $C_{2-8}$ chain can be substituted with one or more than one —OH group). Non-limiting examples include fatty acid diethanolamides (DEA) or fatty acid monoethanolamides (MEA), fatty acid monoisopropanolamides (MIPA), fatty acid diisopropanolamides (DIPA), and fatty acid glucamides (acyl glucamides).

Suitable fatty acid alkanolamides include those formed by reacting an alkanolamine and a C6-C36 fatty acid. Examples include, but are not limited to: oleic acid diethanolamide, myristic acid monoethanolamide, soya fatty acids diethanolamide, stearic acid ethanolamide, oleic acid monoisopropanolamide, linoleic acid diethanolamide, stearic acid monoethanolamide (Stearamide MEA), behenic acid monoethanolamide, isostearic acid monoisopropanolamide (isostearamide MIPA), erucic acid diethanolamide, ricinoleic acid monoethanolamide, coconut fatty acid monoisopropanolamide (cocoamide MIPA), coconut acid monoethanolamide (Cocamide MEA), palm kernel fatty acid diethanolamide, coconut fatty acid diethanolamide, lauric diethanolamide, polyoxyethylene coconut fatty acid monoethanolamide, coconut fatty acid monoethanolamide, lauric monoethanolamide, lauric acid monoisopropanolamide (lauramide MIPA), myristic acid monoisopropanolamide (Myristamide MIPA), coconut fatty acid diisopropanolamide (cocamide DIPA), and mixtures thereof.

In some instances, the fatty acid alkanolamides preferably include cocamide MIPA, cocamide DEA, cocamide MEA, cocamide DIPA, and mixtures thereof. In particular, the fatty acid alkanolamide may be cocamide MIPA, which is commercially available under the tradename EMPILAN from Innospec Active Chemicals.

Fatty acid alkanolamides include those of the following structure:

wherein $R_4$ is an alkyl chain of 4 to 20 carbon atoms ($R_4$ may be, for example, selected from lauric acid, coconut acid, palmitic acid, myristic acid, behenic acid, babassu fatty acid, isostearic acid, stearic acid, corn fatty acid, soy fatty acid, shea butter fatty acids, caprylic acid, capric acid, and mixtures thereof);

$R_6$ is selected from —$CH_2OH$, —$CH_2CH_2OH$, —$CH_2CH_2CH_2OH$, —$CH_2(CHOH)_4CH_2OH$, -benzyl, and mixtures thereof; and $R_6$ is selected from —H, —$CH_3$, —$CH_2OH$, —$CH_2CH_3$, —$CH_2CH_2OH$, —$CH_2CH_2CH_2OH$, —$CH_2(CHOH)_4CH_2OH$, -benzyl, and mixtures thereof.

In some instances, the one or more of the fatty acid alkanolamides include one or more acyl glucamides, for example, acyl glucamides having a carbon chain length of 8 to 20. Non-limiting examples include lauroyl/myristoyl methyl glucamide, capryloyl/capryl methyl glucamide, lauroyl methyl glucamide, myristoyl methyl glucamide, capryloyl methyl glucamide, capryl methyl glucamide, cocoyl methyl glucamide, capryloyl/caproyl methyl glucamide, cocoyl methyl glucamide, lauryl methylglucamide, oleoyl methylglucamide oleate, stearoyl methylglucamide stearate, sunfloweroyl methylglucamide, and tocopheryl succinate methylglucamide.

Water-Soluble Solvent(s)

The hair coloring composition may include a water-soluble solvent. The term "water-soluble solvent" is interchangeable with the term "water-miscible solvent" and means a compound that is liquid at 25° C. and at atmospheric pressure (760 mmHg), and it has a solubility of at least 50% in water under these conditions. In some cases, the water soluble solvents has a solubility of at least 60%, 70%, 80%, or 90%.

Non-limiting examples of water-soluble solvents include, for example, organic solvents selected from glycerin, alcohols (for example, $C_{1-12}$, $C_{1-10}$, $C_{1-8}$, or $C_{1-4}$ alcohols), polyols (polyhydric alcohols), glycols, and a mixture thereof.

As examples of organic solvents, non-limiting mention can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble solvents include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

In some instances, the organic water-soluble solvent is chosen from alcohols, such as ethanol, isopropyl alcohol, benzyl alcohol and phenyl ethyl alcohol; glycols and glycol ethers, such as propylene glycol, hexylene glycol, ethylene glycol monomethyl, monoethyl or monobutyl ether, propylene glycol and its ethers, such as propylene glycol monomethyl ether, butylene glycol, dipropylene glycol, and also diethylene glycol alkyl ethers, such as diethylene glycol monoethyl ether and monobutyl ether; hydrocarbons such as straight chain hydrocarbons, mineral oil, polybutene, hydrogenated polyisobutene, hydrogenated polydecene, polydecene, squalene, petrolatum and isoparaffins; and mixtures, thereof.

Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

In some embodiments, the one or more water-soluble solvents may include those chosen from one or more glycols, C1-6 alcohols, glycerin, and a mixture thereof. For example, the one or more glycols may include those chosen from ethylene glycol, propylene glycol, butylene glycol, hexylene glycol, pentylene glycol, diethylene glycol, dipropylene glycol, 1,3 propanediol, glycerin, and a mixture thereof. In some cases, the water-soluble solvents of the hair coloring composition include or are chosen from propylene glycol, hexylene glycol, and a mixture thereof.

The amount of water-soluble solvents included in the hair-coloring composition may range from about 0.1 to about 25 wt. %, about 0.1 to about 20 wt. %, about 0.1 to about 15 wt. %, about 0.1 to about 10 wt. %, about 0.1 to about 8 wt. %, about 0.1 to about 6 wt. %; from about 0.5 to about 25 wt. % about 0.5 to about 20 wt. %, about 0.5 to about 15 wt. %, about 0.5 to about 10 wt. %, about 0.5 to about 8 wt. %, about 0.5 to 6 wt. %; from about 1 to about 25 wt. %, about 1 to about 20 wt. %, about 1 to about 15 wt. %, about 1 to about 10 wt. %, about 1 to about 8 wt. %, about 1 to about 6 wt. %; from about 1.5 to about 25 wt. %, about 1.5 to about 20 wt. %, about 1.5 to about 15 wt. %, about 1.5 to about 10 wt. %, about 1.5 to about 8 wt. %, about 1.5 to about 6 wt. %; from about 2 to about 25 wt. %, about 2 to about 20 wt. %, about 2 to about 15 wt. %, about 2 to about 10 wt. %, about 2 to about 8 wt. %, about 2 to about 6 wt. %; from about 2.5 to about 25 wt. %, about 2.5 to about 20 wt. %, about 2.5 to about 15 wt. %, about 2.5 to about 10 wt. %, about 2.5 to about 8 wt. %, about 2.5 to about 6 wt. %; from about 3 to about 25 wt. %, about 3 to about 20 wt. %, about 3 to about 15 wt. %, about 3 to about 10 wt. %, about 3 to about 8 wt. %, or about 3 to about 6 wt. %, including ranges and sub-ranges therebetween, based on the total weight of the hair coloring composition.

Alkalizing Agent(s)

The one or more alkalizing agents that may be included in the hair coloring composition can have multiple roles in the coloring process. For instance, the alkalizing agent typically causes the hair shaft to swell, thus allowing the small oxidative dye precursor molecules to more easily penetrate the cuticle and cortex. Also, the alkalize agent can activate the oxidizing agent(s) of the developer composition and contribute to the oxidation condensation process.

The alkalizing agent of the present invention may be chosen from organic amines, organic amine salts, ammonium salts, inorganic bases, and hydroxide base compounds. The organic amines may be chosen from the ones having a pKb at 25° C. of less than 12, such as less than 10 or such as less than 6. It should be noted that this is the pKb corresponding to the function of highest basicity.

Organic amines may be chosen from organic amines comprising one or two primary, secondary, or tertiary amine functions, and at least one linear or branched C1-C8 alkyl groups bearing at least one hydroxyl radical. Organic amines may also be chosen from alkanolamines such as mono-, di- or trialkylamines, comprising one to three identical or different $C_1$-$C_4$ hydroxyalkyl radicals, ethylamines, ethyleneamines, quinoline, aniline and cyclic amines, such as pyrroline, pyrrole, pyrrolidine, imidazole, imidazolidine, imidazolidinine, morpholine, pyridine, piperidine, pyrimidine, piperazine, triazine and derivatives thereof.

The hair coloring composition may include an alkanolamine chosen from monoethanolamine (also known as monoethanolamine or MEA), diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol, 2-amino-2-methyl-1-propanol, and tris(hydroxymethylamino)methane.

Additionally or alternatively, the hair coloring composition may include an amine having a structure represented by the following formula:

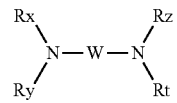

wherein W is chosen from $C_1$-$C_6$ alkylene residues optionally substituted with a hydroxyl group or a $C_1$-$C_6$ alkyl radical; $R_x$, $R_y$, $R_z$, and $R_t$, which may be identical or different, are chosen from a hydrogen atom, $C_1$-$C_6$ alkyl radicals, $C_1$-$C_6$ hydroxyalkyl radicals, and $C_1$-$C_6$ aminoalkyl radicals. Examples of amines having a structure in accordance with the above formula include, but not limited to: 1,3-diaminopropane, 1,3-diamino-2-propanol, spermine, and spermidine.

In some instances, the organic amines are chosen from amino acids. As non-limiting examples, the amino acids may be of natural or synthetic origin, in L, D, or racemic form, and comprise at least one acid function chosen from, for example, carboxylic acid, sulfonic acid, phosphonic acid, and phosphoric acid functions. The amino acids may be in their neutral or ionic form. Further as non-limiting examples, the amino acids may be chosen from basic amino acids comprising an additional amine function optionally included in a ring or in a ureido function. Such basic amino acids may be chosen from those having a structure corresponding to following formula:

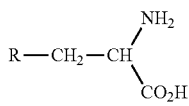

wherein R is a group chosen from:

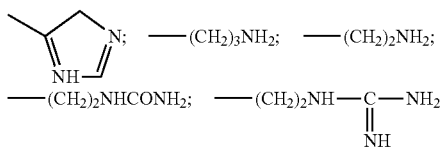

Non-limiting examples of compounds having a structure corresponding to the above formula (A) include histidine, lysine, arginine, ornithine, and citrulline.

In some instances, the amino acids may include or be chosen from aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine, and valine.

The hair coloring composition may include organic amines including, e.g., those chosen from basic amino acids. The amino acids may be chosen from, for instance, arginine, lysine and histidine, or mixtures thereof. In some embodiments, the organic amines are chosen from organic amines of heterocyclic type. Besides histidine that has already been mentioned in the amino acids, non-limiting mention may also be made of pyridine, piperidine, imidazole, 1,2,4-triazole, tetrazole, and benzimidazole. In some embodiments, the organic amines are chosen from amino acid dipeptides. Amino acid dipeptides that may be used in the hair coloring composition include but not limited to: carnosine, anserine, and baleine.

Additionally or alternatively, the organic amines may be chosen from compounds comprising a guanidine function. Organic amines of this type may include, besides arginine that has already been mentioned as an amino acid, creatine, creatinine, 1,1-dimethylguanidine, 1,1-diethylguanidine, glycocyamine, metformin, agmatine, N-amidinoalanine, 3-guanidinopropionic acid, 4-guanidinobutyric acid, and 2-([amino(imino)methyl]amino)ethane-1-sulfonic acid. As a non-limiting example, the organic amines may be chosen from alkanolamines. For example, the organic amines may be chosen from ethanolamine, triethanoloamine, 2-amino-2-methyl-1-propanol (amino methyl propanol), or preferably from 2-amino-2-methyl-1-propanol and monoethanolamine, or mixtures thereof. Further as another example, the organic amine may be monoethanolamine.

The alkalizing agent may be an organic amine in salt form. The term "organic amine salt," as used herein, means organic or mineral salts of an organic amine as described above. As non-limiting examples, the organic salts may be chosen from the salts of organic acids, such as citrates, lactates, glycolates, gluconates, acetates, propionates, fumarates, oxalates and tartrates. As further as non-limiting examples, the mineral salts may be chosen from hydrohalides (for example hydrochlorides), carbonates, hydrogen carbonates, sulfates, hydrogen phosphates, and phosphates.

The hair coloring composition may include alkazing agents in the form of ammonium salts, such as those chosen from the following acid salts: carbonate, bicarbonate. For instance, the salt is the carbonate, such as ammonium carbonate.

The inorganic bases that may be used may be chosen from alkali metal phosphates and carbonates such as, for example, sodium phosphate, potassium phosphate, sodium carbonate, sodium bicarbonate, potassium carbonate, potassium bicarbonate, and their derivatives. The inorganic bases may also include alkali metals of carboxylates such as, for example, sodium acetate, potassium acetate, sodium citrate, and potassium citrate, and their derivatives. Additionally or alternatively, the alkalizing agent may be chosen from at least one hydroxide base compounds, a particularly preferred hydroxide base compounds is ammonium hydroxide.

The hydroxide base compounds can be chosen from alkali metal hydroxides, alkaline-earth metal hydroxides, transition metal hydroxides, quaternary ammonium hydroxides, organic hydroxides, and mixtures thereof. Suitable examples are ammonium hydroxide, sodium hydroxide, potassium hydroxide, lithium hydroxide, rubidium hydroxide, caesium hydroxide, francium hydroxide, beryllium hydroxide, magnesium hydroxide, calcium hydroxide, strontium hydroxide, barium hydroxide, molybdenum hydroxide, manganese hydroxide, zinc hydroxide, cobalt hydroxide, cadmium hydroxide, cerium hydroxide, lanthanum hydroxide, actinium hydroxide, thorium hydroxide, aluminium hydroxide, guanidinium hydroxide and mixtures thereof.

In some instances, the alkalizing agent is chosen from alkali metal carbonates, alkali metal phosphate, organic amines, hydroxide base compounds, and derivatives thereof.

The alkalizing agent may be chosen from aminomethyl propanol, aminomethyl propanediol, triisopropanol amine sodium hydroxide, potassium hydroxide, ammonium hydroxide, dimethylstearylamine, dimethyl/tallowamine lysine, ornithine, arginine, monoethanolamine, triethanolamine, calcium hydroxide, calcium bicarbonate, sodium bicarbonate, ethanolamine and mixtures thereof. For example, the alkalizing agent comprises ammonium hydroxide and ethanolamine.

The amount of the alkalizing agent in the composition can be such that the pH of the composition can be neutral or alkaline range pH above 7. For example, the total amount of alkalizing agent(s) in the hair coloring composition can vary but in some cases may be about 0.1 to about 40 wt. %, based on the total weight of the hair coloring composition. In some cases, the total amount of the one or more alkalizing agents is about 0.1 to about 25 wt. %, about 0.1 to about 20 wt. %, about 0.1 to about 15 wt. %, about 0.1 to about 10 wt. %, about 0.1 to about 8 wt. %, about 0.1 to about 6 wt. %; from about 0.5 to about 25 wt. % about 0.5 to about 20 wt. %, about 0.5 to about 15 wt. %, about 0.5 to about 10 wt. %, about 0.5 to about 8 wt. %, about 0.5 to 6 wt. %; from about 1 to about 25 wt. %, about 1 to about 20 wt. %, about 1 to about 15 wt. %, about 1 to about 10 wt. %, about 1 to about 8 wt. %, about 1 to about 6 wt. %; from about 1.5 to about 25 wt. %, about 1.5 to about 20 wt. %, about 1.5 to about 15 wt. %, about 1.5 to about 10 wt. %, about 1.5 to about 8 wt. %, about 1.5 to about 6 wt. %; from about 2 to about 25 wt. %, about 2 to about 20 wt. %, about 2 to about 15 wt. %, about 2 to about 10 wt. %, about 2 to about 8 wt. %, about 2 to about 6 wt. %; from about 2.5 to about 25 wt. %, about 2.5 to about 20 wt. %, about 2.5 to about 15 wt. %, about 2.5 to about 10 wt. %, about 2.5 to about 8 wt. %, about 2.5 to about 6 wt. %; from about 3 to about 25 wt. %, about 3 to about 20 wt. %, about 3 to about 15 wt. %, about 3 to about 10 wt. %, about 3 to about 8 wt. %, or about 3 to about 6 wt. %, including ranges and sub-ranges therebetween, based on the total weight of the hair coloring composition.

The hair coloring compositions may contain a small amount (i.e., greater than 0 but less than 8, 7, 6, 5, 4, 3 or 2% by weight) of ammonia, or is substantially free of ammonia.

Cationic Conditioning Polymer(s)

The hair coloring composition may include one or more cationic conditioning polymers. The cationic conditioning polymers can comprise mixtures of monomer units derived from amine- and/or quaternary ammonium-substituted monomer and/or compatible spacer monomers.

Suitable cationic conditioning polymers include, for example: copolymers of 1-vinyl-2-pyrrolidine and 1-vinyl-3-methyl-imidazolium salt (e.g., Chloride salt) (referred to as Polyquaternium-16) such as those commercially available from BASF under the LUVIQUAT tradename (e.g., LUVIQUAT FC 370); copolymers of 1-vinyl-2-pyrrolidine and dimethylaminoethyl methacrylate (referred to as Polyquaternium-11) such as those commercially available from Gar Corporation (Wayne, N.J., USA) under the GAFQUAT tradename (e.g., GAFQUAT 755N); and cationic diallyl quaternary ammonium-containing polymer including, for example, dimethyldiallyammonium chloride homopolymer and copolymers of acrylamide and dimethyldiallyammonium chloride (referred to as Polyquaternium-6 and Polyquaternium-7).

Other cationic conditioning polymers that may be used include polysaccharide polymers, such as cationic cellulose derivatives and cationic starch derivatives. Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide (referred to as Polyquaternium-10). Another type of cationic cellulose includes the polymeric quaternary ammonium salts of hydroxyethyl cellulose reacted with lauryl dimethyl ammonium-substituted epoxide (referred to as Polyquaternium-24). These materials are available from Amerchol Corp. (Edison, N.J., USA) under the tradename Polymer LM-200. Additionally or alternatively, the cationic conditioning polymers may include or be chosen from cationic guar gum derivatives, such as guar hydroxypropyltrimonium chloride.

The hair coloring composition may include or be chosen from polyquaterniums. For example, the coloring composition may include Polyquaternium-1 (ethanol, 2,2',2"-nitrilotris-, polymer with 1,4-dichloro-2-butene and N,N,N',N'-tetramethyl-2-butene-1,4-diamine), Polyquaternium-2, (poly[bis(2-chloroethyl) ether-alt-1,3-bis[3-(dimethylamino)propyl]urea]), Polyquaternium-4, (hydroxyethyl cellulose dimethyl diallylammonium chloride copolymer; Diallyldimethylammonium chloride-hydroxyethyl cellulose copolymer), Polyquaternium-5 (copolymer of acrylamide and quaternized dimethylammoniumethyl methacrylate), polyquaternium-6 (poly(diallyldimethylammonium chloride)), Polyquaternium-7 (copolymer of acrylamide and diallyldimethylammonium chloride), Polyquaternium-8 (copolymer of methyl and stearyl dimethylaminoethyl ester of methacrylic acid, quaternized with dimethylsulphate), Polyquaternium-9 (homopolymer of N,N-(dimethylamino)ethyl ester of methacrylic acid, quaternized with bromomethane), Polyquaternium-10 (quaternized hydroxyethyl cellulose), polyquaternium-11 (copolymer of vinylpyrrolidone and quaternized dimethylaminoethyl methacrylate), Polyquaternium-12 (ethyl methacrylate/abietyl methacrylate/diethylaminoethyl methacrylate copolymer quaternized with dimethyl sulfate), Polyquaternium-13 (ethyl methacrylate/oleyl methacrylate/diethylaminoethyl methacrylate copolymer quaternized with dimethyl sulfate), Polyquaternium-14 (trimethylaminoethylmethacrylate homopolymer), Polyquaternium-15 (acrylamide-dimethylaminoethyl methacrylate methyl chloride copolymer), Polyquaternium-16 (copolymer of vinylpyrrolidone and quaternized vinylimidazole), Polyquaternium-17 (adipic acid, dimethylaminopropylamine and dichloroethylether copolymer), Polyquaternium-18 (azelanic acid, dimethylaminopropylamine and dichloroethylether copolymer), Polyquaternium-19 (copolymer of polyvinyl alcohol and 2,3-epoxypropylamine), Polyquaternium-20 (copolymer of polyvinyl octadecyl ether and 2,3-epoxypropylamine), Polyquaternium-22 (copolymer of acrylic acid and diallyldimethylammonium chloride), Polyquaternium-24 (auaternary ammonium salt of hydroxyethyl cellulose reacted with a lauryl dimethyl ammonium substituted epoxide), Polyquaternium-27 (block copolymer of Polyquaternium-2 and Polyquaternium-17), Polyquaternium-28 (copolymer of vinylpyrrolidone and methacrylamidopropyl trimethylammonium), Polyquaternium-29 (chitosan modified with propylen oxide and quaternized with epichlorhydrin), Polyquaternium-30 (ethanaminium, N-(carboxymethyl)-N,N-dimethyl-2-[(2-methyl-1-oxo-2-propen-1-yl)oxy]-, inner salt, polymer with methyl 2-methyl-2-propenoate), Polyquaternium-31 (N,N-dimethylaminopropyl-N-acrylamidine quatemized with diethylsulfate bound to a block of polyacrylonitrile), Polyquaternium-32 (poly(acrylamide 2-methacryloxyethyltrimethyl ammonium chloride)), Polyquaternium-33 (copolymer of trimethylaminoethylacrylate salt and acrylamide), Polyquaternium-34 (copolymer of 1,3-dibromopropane and N,N-diethyl-N',N'-dimethyl-1,3-propanediamine), Polyquaternium-35 (methosulphate of the copolymer of methacryloyloxyethyltrimethylammoniurn and of methacryloyloxyethyldimethylacetylammonium), Polyquaternium-36 (copolymer of N,N-dimethylaminoethylmethacrylate and buthylmethacrylate, quaternized with dimethylsulphate), Polyquaternium-37 (poly(2-methacryloxyethyltrimethylammonium chloride)), Polyquaternium-39 (terpolymer of acrylic acid, acrylamide and diallyldimethylammonium Chloride), Polyquaternium-42 (poly[oxyethylene(dimethylimino)ethylene (dimethylimino)ethylene dichloride]), Polyquaternium-43 (copolymer of acrylamide, acrylamidopropyltrimonium chloride, 2-amidopropylacrylamide sulfonate and dimethylaminopropylamine), Polyquaternium-44 (3-Methyl-1-vinylimidazolium methyl sulfate-N-vinylpyrrolidone copolymer), Polyquaternium-45 (copolymer of (N-methyl-N-ethoxyglycine)methacrylate and N,N-dimethylaminoethylmethacrylate, quaternized with dimethyl sulphate), Polyquaternium-46 (terpolymer of vinylcaprolactam, vinylpyrrolidone, and quaternized vinylimidazole), and Polyquaternium-47 (terpolymer of acrylic acid, methacrylamidopropyl trimethylammonium chloride, and methyl acrylate).

In some instances, the hair coloring compositions of the instant disclosure include one or more cationic conditioning polymers selected from cationic cellulose derivatives, quaternized hydroxyethyl cellulose (e.g., polyquaternium-10), cationic starch derivatives, cationic guar gum derivatives, copolymers of acrylamide and dimethyldiallyammonium chloride (e.g., polyquaternium-7), polyquaterniums, and a mixture thereof. In one particularly preferred embodiment, the cationic conditioning polymer(s) are selected from polyquaterniums, for example, polyquaterniums selected from polyquaternium-4, polyquaternium-5, polyquaternium-6, polyquaternium-7, polyquaternium-10, polyquaternium-22, polyquaternium-37, polyquaternium-39, polyquaternium-47, polyquaternium-53, and a mixture thereof. A combination of two or more polyquaterniums can be useful. In some embodiments, the one or more cationic conditioning polymers of the hair coloring composition includes or is chosen from polyquaterniurn-6.

The hair coloring compositions can, in some instances include, conditioning agents such as polyalkyl siloxane, polyaryl siloxane, polyalkylaryl siloxane, polyether siloxane copolymer, polydimethyl siloxane, a polydiethyl siloxane, a polydipropyl siloxane, a polymethylethyl siloxane, a polymethylpropylsiloxane, a polymethylphenylsiloxane, or a mixture thereof.

The amount of conditioning agents in the hair coloring composition typically ranges from about 0.1 to about 20 wt. % of the total weight of the hair coloring composition. In some instances, the conditioning agents are in an amount ranging from about 0.1 to about 20 wt. %, about 0.1 to about 15 wt. %, about 0.1 to about 10 wt. %, about 0.1 to about 8 wt. %, about 0.1 to about 6 wt. %; from about 0.5 to about 25 wt. % about 0.5 to about 20 wt. %, about 0.5 to about 15 wt. %, about 0.5 to about 10 wt. %, about 0.5 to about 8 wt. %, about 0.5 to 6 wt. %; from about 1 to about 25 wt. %, about 1 to about 20 wt. %, about 1 to about 15 wt. %, about 1 to about 10 wt. %, about 1 to about 8 wt. %, about 1 to about 6 wt. %; from about 1.5 to about 25 wt. %, about 1.5 to about 20 wt. %, about 1.5 to about 15 wt. %, about 1.5 to about 10 wt. %, about 1.5 to about 8 wt. %, or about 1.5 to about 6 wt. %, including ranges and sub-ranges therebetween, based on the total weight of the hair coloring composition.

Fatty Alcohols

Optionally, the hair coloring compositions may include one or more fatty alcohols. Examples of fatty alcohols include those having from about 8 to about 30 carbon atoms, from about 12 to about 22 carbon atoms, and from about 14 to about 22 carbon atoms. These fatty alcohols can be straight or branched chain alcohols and can be saturated or unsaturated. Non-limiting examples of fatty alcohols include decyl alcohol, undecyl alcohol, dodecyl alcohol, myristyl alcohol, lauryl alcohol, cetyl alcohol, stearyl alcohol, isostearyl alcohol, isocetyl alcohol, behenyl alcohol, linalool, oleyl alcohol, cis4-t-butylcyclohexanol, myricyl alcohol and a mixture thereof. In some cases, the fatty alcohols comprise at least one of or may be chosen from myristyl alcohol, lauryl alcohol, cetyl alcohol, stearyl alcohol, isostearyl alcohol, oleyl alcohol, isotridecyl alcohol, and a mixture thereof. In some embodiments, the hair coloring composition includes fatty alcohol(s) chosen from myristyl alcohol, lauryl alcohol, cetyl alcohol, and a mixture thereof.

The saturated liquid fatty alcohols may be branched and optionally contain in their structure at least one aromatic or non-aromatic ring. In some instances, however, the fatty alcohols are acyclic. Non-limiting examples of liquid saturated fatty alcohols include octyldodecanol, isostearyl alcohol, and 2-hexyldecanol.

The unsaturated liquid fatty alcohol may include in their structure at least one double or triple bond. For example, the fatty alcohols may include several double bonds (such as 2 or 3 double bond), which may be conjugated or non-conjugated. The unsaturated fatty alcohols can be linear or branched and may be acyclic or include in their structure at least one aromatic or non-aromatic ring. Liquid unsaturated fatty alcohols may include or be chosen from oleyl alcohol, linoleyl alcohol, linolenyl alcohol and undecylenyl alcohol.

Non-limiting examples of solid fatty alcohols include linear or branched, saturated or unsaturated alcohols containing from 8 to 30 carbon atoms, for example, myristyl alcohol, cetyl alcohol, stearyl alcohol and their mixture, cetylstearyl alcohol.

The fatty alcohols, if present, may be include in the hair care compositions in an amount ranging from about 0.1 to about 25 wt. %, about 0.1 to about 20 wt. %, about 0.1 to about 15 wt. %, about 0.1 to about 10 wt. %, about 0.1 to about 8 wt. %, about 0.1 to about 6 wt. %; from about 0.5 to about 25 wt. % about 0.5 to about 20 wt. %, about 0.5 to about 15 wt. %, about 0.5 to about 10 wt. %, about 0.5 to about 8 wt. %, about 0.5 to 6 wt. %; from about 1 to about 25 wt. %, about 1 to about 20 wt. %, about 1 to about 15 wt. %, about 1 to about 10 wt. %, about 1 to about 8 wt. %, about 1 to about 6 wt. %; from about 1.5 to about 25 wt. %, about 1.5 to about 20 wt. %, about 1.5 to about 15 wt. %, about 1.5 to about 10 wt. %, about 1.5 to about 8 wt. %, about 1.5 to about 6 wt. %; from about 2 to about 25 wt. %, about 2 to about 20 wt. %, about 2 to about 15 wt. %, about 2 to about 10 wt. %, about 2 to about 8 wt. %, about 2 to about 6 wt. %; from about 2.5 to about 25 wt. %, about 2.5 to about 20 wt. %, about 2.5 to about 15 wt. %, about 2.5 to about 10 wt. %, about 2.5 to about 8 wt. %, about 2.5 to about 6 wt. %; from about 3 to about 25 wt. %, about 3 to about 20 wt. %, about 3 to about 15 wt. %, about 3 to about 10 wt. %, about 3 to about 8 wt. %, or about 3 to about 6 wt. %, including ranges and sub-ranges therebetween, based on the total weight of the hair coloring composition.

In some instances, however, the hair coloring composition has less than 5 wt. %, preferably less than 3 wt. %, preferably less than 1 wt. %, of fatty alcohols. In another embodiment, the hair coloring composition is free of or essentially free of fatty alcohols.

Water

The total amount of water in the hair coloring composition can vary, but is typically about 30 to about 95 wt. %, based on the total weight of the hair coloring composition. In some instances, total amount of water is about 30 to about 90 wt. %, about 30 to about 85 wt. %, about 30 to about 80 wt. %; from about 35 to about 90 wt. %, about 35 to about 85 wt. %, about 35 to about 80 wt. %; from about 40 to about 90 wt. %, about 40 to about 85 wt. %, about 40 to about 80 wt. %; from about 45 to about 90 wt. %, about 45 to about 85 wt. %, about 45 to about 80 wt. %; from about 50 to about 90 wt. %, about 50 to about 85 wt. %, about 50 to about 80 wt. %; from about 55 to about 90 wt. %, about 55 to about 85 wt. %, about 55 to about 80 wt. %; from about 60 to about 90 wt. %, about 60 to about 85 wt. %, about 60 to about 80 wt. %, from about 65 to about 90 wt. %, about 65 to about 85 wt. %, about 65 to about 80 wt. %; from about 70 to about 90 wt. %, about 70 to about 85 wt. %, or about 70 to about 80 wt. %, including ranges and sub-ranges therebetween, of the total weight of the hair coloring composition.

pH Adjuster(s)

The hair coloring composition may include one or more pH adjusters to increase or decrease the overall pH of the hair coloring composition. For example, one or more acids may be included to decrease the pH of the hair coloring composition. Examples of suitable acids for decreasing the pH of the hair coloring composition include, but are not limited to, citric acid, acetic acid, and the like. The hair coloring composition may include one or more bases, such as sodium hydroxide, potassium hydroxide and the like, to decrease the pH of the hair coloring composition. Additional or alternative acids and bases that are suitable for adjusting the pH of the hair coloring composition are readily known to one of ordinary skill in the art.

The amount of the pH adjuster in the hair coloring composition may be based on the desired pH of the final hair coloring composition and/or product. For example, the total amount of the pH adjuster may range from about 0.05 to about 20 wt. %, based on the total weight of the hair coloring composition. In some instances, the total amount of pH adjuster is from about 0.05 to about 15 wt. %, about 0.5 to about 10 wt. %, about 1 to about 5 wt. %, about 1.5 to about 4 wt. %, or about 2.0 to about 3 wt. %, based on the total weight of the hair coloring composition, including ranges and sub-ranges therebetween. Additionally or alternatively, the hair coloring composition may include an amount of pH adjuster ranging from 0.05 to 15 wt. %, 0.5 to 10 wt. %, 1 to 5 wt. %, 1.5 to 4 wt. %, or 2.0 to 3 wt. %, based on the total weight of the hair coloring composition, including ranges and sub-ranges therebetween.

Thickening Agent(s)

The hair coloring compositions described herein may include one or more thickening agents. The amount of thickening agents may depend on the other components in hair coloring composition and desired viscosity for the hair coloring composition. For example, the hair coloring composition may include an amount of thickening agents such that the viscosity of the hair coloring composition is about 1,000 cP to about 100,000 cP, about 5,000 cP to about 50,000 cP, about 10,000 to about 50,000 cP, or about 15,000 cP to about 45,000 cP at a temperature of 25° C. using a Brookfield rheometer with a spindle number 5 at 20 revolutions per minute (RPM). Additionally or alternatively, the viscosity of the hair coloring composition may be 1,000 cP to 100,000 cP, 5,000 cP to 50,000 cP, 10,000 to 50,000 cP, or 15,000 cP to 45,000 cP at a temperature of 25° C. using a Brookfield rheometer with a spindle number 5 at 20 RPM.

The thickening agents may be in an amount of about 0.1 to about 20 wt. %, about 0.1 to about 10 wt. %, about 0.1 to about 9 wt. %, about 0.2 to about 9 wt. %, about 0.3 to about 9 wt. %, about 0.4 to about 8 wt. %, about 0.5 to about 5 wt. %, about 1 to about 20 wt. %, about 1 to about 5 wt. %, or about 1 to about 3 wt. %, including ranges and sub-ranges therebetween, based on the total weight of the hair coloring composition. Additionally or alternatively, the thickening agents may be in an amount of 0.1 to 20 wt. %, 0.1 to 10 wt. %, 0.1 to 9 wt. %, 0.2 to 9 wt. %, 0.3 to 9 wt. %, 0.4 to 8 wt. %, 0.5 to 5 wt. %, 1 to 20 wt. %, 1 to 5 wt. %, or 1 to 3 wt. %, including ranges and sub-ranges therebetween, based on the total weight of the hair coloring composition. Further, the amount of thickening agent(s) may be from 0.1, 0.2, 0.3, 0.4, 0.5, 0.6, 0.7, 0.8, 0.9, 1.0, or 1.5 wt. % to 2, 3, 4, 5, 6, 7, 8, 9, 10, 15, or 20 wt. %, including ranges and sub-ranges therebetween, based on the total weight of the hair coloring composition.

The one or more thickening agent may be xanthan gum, guar gum, biosaccharide gum, cellulose, acacia Seneca gum, sclerotium gum, agarose, pechtin, gellan gum, hyaluronic acid. Additionally, the one or more thickening agent may include polymeric thickeners chosen from ammonium polyacryloyldimethyl taurate, ammonium acryloyldimethyltaurate/VP copolymer, sodium polyacrylate, acrylates copolymers, polyacrylamide, carbomer, and acrylates/C10-30 alkyl acrylate crosspolymer. In some instances, the hair coloring composition includes ammonium polyacryloyldimethyl taurate and/or sodium polyacrylate. In another instance, hair coloring composition includes at least one or is chosen from ammonium polyacryloyldimethyl taurate, xanthan gum, carbomer, and a mixture thereof.

Many thickening agents are water-soluble, and increase the viscosity of water or form an aqueous gel when the hair coloring composition of the disclosure is dispersed/dissolved in water. The aqueous solution may be heated and cooled, or neutralized, for forming the gel, if necessary. The thickener may be dispersed/dissolved in an aqueous solvent that is soluble in water, e.g., ethyl alcohol when it is dispersed/dissolved in water. Non-limiting examples of various types of thicken agents include:

Carboxylic Acid Polymers

In some instances, carboxylic acid polymer may be used in the hair coloring composition. Carboxylic acid polymer are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. Examples of carboxylic acid polymers that may, in some instances, be included in the hair coloring compositions include one or more of or may be chosen from carbomers, which are homopolymers of acrylic acid crosslinked with allyl ethers of sucrose or pentaerytritol.

Commercially available carbomers include Carbopol® 900 series from B.F. Goodrich (e.g., Carbopol® 954). In addition, other suitable carboxylic acid polymeric agents include Ultrez® 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as Carbopol® 1342, Carbopol® 1382, Pemulen TR-1, and Pemulen TR-2, from B.F. Goodrich. In other words, examples of carboxylic acid polymer thickeners useful herein are those selected from carbomers, acrylates/C10-C30 alkyl acrylate crosspolymers, and mixtures thereof.

Crosslinked Polyacrylate Polymers

The hair coloring compositions can optionally contain crosslinked polyacrylate polymers useful as thickeners or gelling agents including both cationic and nonionic polymers. Examples of crosslinked nonionic polyacrylate polymers and crosslinked cationic polyacrylate polymers that may be useful in some instances are those described in U.S. Pat. Nos. 5,100,660, 4,849,484, 4,835,206, 4,628,078 4,599, 379 and EP 228,868, which are all incorporated herein by reference in their entirety.

Polyacrylamide Polymers

The hair coloring compositions can optionally contain polyacrylamide polymers, such as nonionic polyacrylamide polymers including substituted branched or unbranched polymers. Among these polyacrylamide polymers is the nonionic polymer given the CTFA designation polyacrylamide and isoparaffin and laureth-7, available under the Tradename Sepigel 305 from Seppic Corporation. Other polyacrylamide polymers that may be included in the hair coloring composition include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc. In some instances, the hair coloring composition includes thickening and texturizing gels of the type as exemplified by the product range called Lubrajel® from United Guardian. These gels have moisturizing, viscosifying, stabilizing properties.

Polysaccharides

In some instances, polysaccharides may be used in the hair coloring composition as a gelling agent. "Polysaccharides" refer to gelling agents that contain a backbone of repeating sugar (i.e., carbohydrate) units. Nonlimiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation. Other useful polysaccharides include scleroglucans comprising a linear chain of (1-3) linked glucose units with a (1-6) linked glucose every three units, a commercially available example of which is Clearogel™ CS11 from Michel Mercier Products Inc.

Gums

Other thickening and gelling agents that may be used, in some instances, include gums, which may be primarily derived from natural sources. Non-limiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

Additional examples of water-soluble thickeners include water-soluble natural polymers, water-soluble synthetic polymers, clay minerals, and silicic anhydride. Non-limiting examples of water-soluble natural polymers include gum arabic, tragacanth gum, karaya gum, guar gum, gellan gum, tara gum, locust bean gum, tamarind gum, sodium alginate, alginic acid propyleneglycol ester, carrageenan, farcelluran, agar, high-methoxy pectin, low-methoxy pectin, xanthine, chitosan, starch (for example starch derived from corn, potato, wheat, rice, sweet potato and tapioca, a-starch, soluble starch), fermentation polysaccharide (for example, xanthan gum, pullulan, carciran, dextran), acidic heteropolysaccharide derived from callus of plants belonging to Polyantes sp. (for example, tuberous polysaccharide), proteins (for example, sodium casein, gelatin, albumin), chondroitin sulfate, and hyaluronic acid.

The hair coloring composition may include water-soluble synthetic polymers including, e.g., polyvinyl alcohol, sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt), and starch derivatives (for example, starch oxide, dialdehyde starch, dextrin, British gum, acetyl starch, starch phosphate, carboxymethyl starch, hydroxyethyl starch, hydroxypropyl starch).

The hair coloring compositions disclosed herein may be incorporated into a kit. For example, a kit for coloring hair may include a hair coloring composition as discussed herein and an aqueous developer composition comprising one or more peroxides.

The present disclosure is also directed to methods for coloring hair. In some instances, the method includes mixing a hair coloring composition in accordance with the disclosure herein with an aqueous developer composition comprising one or more peroxides; applying the mixture onto hair and allowing the mixture to remain on the hair for about 1 to about 45 minutes; and rinsing the mixture from hair. The hair coloring compositions can be applied to the wet or damp hair and may be massaged into the hair, for example, with the hands, and/or spread throughout the hair with a comb or brush. In addition to providing vibrant color to the hair, the methods may result in a smoothing and softening of the hair, which reduces frizz, dryness, and unwanted volume.

Embodiments

In certain embodiments, the hair coloring composition of the instant disclosure optionally form a microemulsion and include:

about 0.1 to about 10 wt. %, preferably about 0.5 to about 8 wt. %, more preferably about 0.8 to about 6 wt. %, of one or more oxidative dye precursors;

about 0.1 to about 15 wt. %, preferably about 0.5 to about 10 wt. %, more preferably, about 1 to about 6 wt. %, of one or more anionic surfactants chosen from acyl amino acid surfactants, the acyl amino acid surfactants preferably being chosen from acyl glycinates, such as sodium cocoyl glycinate, sodium lauroyl glycinate, sodium myristoyl glycinate, potassium lauroyl glycinate, potassium cocoyl glycinate, and a mixture thereof;

about 0.1 to about 15 wt. %, preferably about 0.5 to about 10 wt. %, more preferably about 1 to about 6 wt. %, of one or more amphoteric surfactants, such as those chosen from chosen from betaines, alkyl sultaines, alkyl amphoacetates, alkyl amphoproprionates, salts thereof, and a mixture thereof, the amphoteric surfactant preferably including one or more betaines chosen from coco betaine, cocamidopropyl betaine, lauryl betaine, laurylhydroxy sulfobetaine, lauryldimethyl betaine, cocamidopropyl hydroxysultaine, behenyl betaine, capryl/capramidopropyl betaine, lauryl hydroxysultaine, stearyl betaine, and mixtures thereof;

about 0.1 to about 30 wt. %, preferably about 0.5 to about 20 wt. %, more preferably about 1 to about 15 wt. %, of a plurality of nonionic surfactants, the nonionic surfactant compositions including at least the following compounds;

(i) about 0.1 to about 15 wt. %, preferably about 0.5 to about 10 wt. %, more preferably about 1 to about 8 wt. %, of one or more alkyl polyglucosides, such as those chosen from lauryl glucoside, octyl glucoside, decyl glucoside, coco glucoside, caprylyl/capryl glucoside, sodium lauryl glucose carboxylate, and a mixture thereof;

(ii) about 0.1 to about 15 wt. %, preferably about 0.5 to about 10 wt. %, more preferably about 1 to about 6 wt. % of a sorbitan compound, a derivative thereof, or a mixture thereof, such as at least one polysorbate chosen from polysorbate-20 (POE(20) sorbitan monolaurate), polysorbate-21 (POE(4) sorbitan monolaurate), polysorbate-40 (POE(20) sorbitan monopalmitate), polysorbate-60 (POE(20) sorbitan monostearate), polysorbate-61 (POE(4) sorbitan monostearate), polysorbate-65 (POE(20) sorbitan tristearate), polysorbate-80 (POE (20)sorbitan monooleate), polysorbate-81 (POE(4) sorbitan monooleate), polysorbate 85 (POE(20) Sorbitan Trioleate), and a mixture thereof; and (iii) about 0.1 to about 10 wt. %, preferably about 0.5 to about 8 wt. %, more preferably about 0.8 to 6 wt. % of one or more polyol esters, such as alkoxylated polyol esters preferably chosen from PEG-55 propylene glycol oleate, PEG-6 propylene glycol caprylate/caprate, PEG-8 propylene glycol cocoate, PEG-25 propylene glycol stearate, and PEG-120 propylene glycol stearate, and a mixture thereof.

In other embodiments, the hair coloring composition of the instant disclosure optionally form a microemulsion and include:

about 0.1 to about 10 wt. %, preferably about 0.5 to about 8 wt. %, more preferably about 0.8 to about 6 wt. %, of one or more oxidative dye precursors;

about 0.1 to about 15 wt. %, preferably about 0.5 to about 10 wt. %, more preferably, about 1 to about 6 wt. %, of one or more anionic surfactants chosen from acyl amino acid surfactants, the acyl amino acid surfactants preferably being chosen from acyl glycinates, such as sodium cocoyl glycinate, sodium lauroyl glycinate, sodium myristoyl glycinate, potassium lauroyl glycinate, potassium cocoyl glycinate, and a mixture thereof;

about 0.1 to about 15 wt. %, preferably about 0.5 to about 10 wt. %, more preferably about 1 to about 6 wt. %, of one or more amphoteric surfactants, such as those chosen from chosen from betaines, alkyl sultaines, alkyl amphoacetates, alkyl amphoproprionates, salts thereof, and a mixture thereof, the amphoteric surfactant preferably including one or more betaines chosen from coco betaine, cocamidopropyl betaine, lauryl betaine, laurylhydroxy sulfobetaine, lauryldimethyl betaine, cocamidopropyl hydroxysultaine, behenyl betaine, capryl/capramidopropyl betaine, lauryl hydroxysultaine, stearyl betaine, and mixtures thereof;

about 0.1 to about 30 wt. %, preferably about 0.5 to about 20 wt. %, more preferably about 1 to about 15 wt. %, of a plurality of nonionic surfactants, the nonionic surfactant compositions including at least the following compounds;

(i) about 0.1 to about 15 wt. %, preferably about 0.5 to about 10 wt. %, more preferably about 1 to about 8 wt. %, of one or more alkyl polyglucosides, such as those chosen from lauryl glucoside, octyl glucoside, decyl glucoside, coco glucoside, caprylyl/capryl glucoside, sodium lauryl glucose carboxylate, and a mixture thereof;

(ii) about 0.1 to about 15 wt. %, preferably about 0.5 to about 10 wt. %, more preferably about 1 to about 6 wt. % of a sorbitan compound, a derivative thereof, or a mixture thereof, such as at least one polysorbate chosen from polysorbate-20 (POE(20) sorbitan monolaurate), polysorbate-21 (POE(4) sorbitan monolaurate), polysorbate-40 (POE(20) sorbitan monopalmitate), polysorbate-60 (POE(20) sorbitan monostearate), polysorbate-61 (POE(4) sorbitan monostearate), polysorbate-65 (POE(20) sorbitan tristearate), polysorbate-80 (POE(20)sorbitan monooleate), polysorbate-81 (POE(4) sorbitan monooleate), polysorbate 85 (POE(20) Sorbitan Trioleate), and a mixture thereof;

(iii) about 0.1 to about 10 wt. %, preferably about 0.5 to about 8 wt. %, more preferably about 0.8 to 6 wt. % of one or more polyol esters, such as alkoxylated polyol esters preferably chosen from PEG-55 propylene glycol oleate, PEG-6 propylene glycol caprylate/caprate, PEG-8 propylene glycol cocoate, PEG-25 propylene glycol stearate, and PEG-120 propylene glycol stearate, and a mixture thereof.

one or more water-soluble solvents, such as those chosen from one or more glycols, $C_{1-6}$ alcohols, glycerin, and a mixture thereof, the one or more glycols, if present, preferably being chosen from ethylene glycol, propylene glycol, butylene glycol, hexylene glycol, pentylene glycol, diethylene glycol, dipropylene glycol, 1,3 propanediol, glycerin, and a mixture thereof;

one or more alkalizing agents chosen from alkali metal carbonates, alkali metal phosphates, organic amines, hydroxide base compounds, and mixtures thereof, and preferably chosen from ammonium hydroxide, ethanolamine and mixtures thereof; and one or more cationic conditioning polymers, such as those chosen from polyquaterniums, including, e.g., polyquaternium-6.

In yet additional embodiments, the hair coloring composition of the instant disclosure optionally form a microemulsion and include:

about 0.1 to about 10 wt. %, preferably about 0.5 to about 8 wt. %, more preferably about 0.8 to about 6 wt. %, of one or more oxidative dye precursors;

about 0.1 to about 15 wt. %, preferably about 0.5 to about 10 wt. %, more preferably, about 1 to about 6 wt. %, of sodium cocoyl glycinate;

about 0.1 to about 15 wt. %, preferably about 0.5 to about 10 wt. %, more preferably about 1 to about 6 wt. %, of cocamidopropyl betaine;

about 0.1 to about 30 wt. %, preferably about 0.5 to about 20 wt. %, more preferably about 1 to about 15 wt. %, of a plurality of nonionic surfactants, the nonionic surfactant compositions including at least the following compounds;

(i) about 0.1 to about 15 wt. %, preferably about 0.5 to about 10 wt. %, more preferably about 1 to about 8 wt. %, of lauryl glucoside;

(ii) about 0.1 to about 15 wt. %, preferably about 0.5 to about 10 wt. %, more preferably about 1 to about 6 wt. % of polysorbate-21; and (iii) about 0.1 to about 10 wt. %, preferably about 0.5 to about 8 wt. %, more preferably about 0.8 to 6 wt. % of PEG-55 propylene glycol oleate; and about 30 to about 95 wt. % of water.

EXAMPLES

Six hair coloring compositions (i.e., Exemplary Compositions A and B and Comparative Compositions C-F) were prepared according to the following formulations. During the preparation, Exemplary Compositions A and B were heated to maximum temperature of 65° C. Comparative Examples C and D were heated during preparation to a maximum temperature of 25° C. Comparative Example E was heated during preparation to a maximum temperature of 30° C. Comparative Example F was prepared similar to Examplary compositions A and B.

|   |   |   | INCI US | Inventive A | Inventive B | Comparative C | D | E | F |
|---|---|---|---|---|---|---|---|---|---|
| a | Oxidative Dye Precursors | | p-PHENYLENEDIAMINE, RESORCINOL, p-AMINOPHENOL, HYDROXYPROPYL BIS(N-HYDROXYETHYL-P-PHENYLENEDIAMINE) HCL, 4-AMINO-2-HYDROXYTOLUENE, m-AMINOPHENOL, AND 2,4-DIAMINOPHENOXYETHANOL HCL | 2.02 | 2.02 | 2.02 | 2.02 | 2.02 | 2.02 |
| b | Anionic Surfactant | | SODIUM COCOYL GLYCINATE | 1.5 | 1.5 | 1.5 | 1.5 | 1.5 | 3 |
| c | Amphoteric Surfactant | | COCAMIDOPROPYL BETAINE | 2.3 | 1.9 | 1.9 | | 1.9 | 5.7 |
| d | i | Nonionic Surfactants Polyglucoside | LAURYL GLUCOSIDE | 3.9 | 3.3 | | | 3.3 | 7.2 |
|   | ii | Polysorbate | POLYSORBATE 21 | 2.4 | 2.4 | 2.4 | 2.4 | 2.4 | |
|   | iii | Polyol Ester | PEG-55 PROPYLENE GLYCOL OLEATE | 0.6 | 0.6 | 0.6 | 0.6 | 0.6 | 1.4 |
| f | Water-Soluble Solvent | | PROPYLENE GLYCOL AND HEXYLENE GLYCOL | 3.6 | 3.6 | 3.6 | 3.6 | 3.6 | 1.7 |
| g | Alkalizing Agent | | AMMONIUM HYDROXIDE | 4.2 | 4.2 | 4.2 | 4.2 | 4.2 | 4.2 |
| h | Cationic Conditioning Polymers | | POLYQUATERNIUM-6 | | 1.4 | 1.4 | 1.4 | 1.4 | |
|   | Alkoxylated Fatty Alcohol | | DECETH-3 | | | 6.9 | 6.9 | 6.9 | |
|   | Fatty Alcohol | | CETYL ALCOHOL, LAURYL ALCOHOL, AND/OR MYRISTYL ALCOHOL | | | 5.1 | 5.1 | | |
|   | Salt | | SODIUM CHLORIDE | 0.4 | 0.4 | 0.4 | | 0.4 | 1.1 |
|   | Antioxidant/Fragrance | | ERYTHORBIC ACID | 0.3 | 0.3 | 0.3 | 0.3 | 0.3 | 0.3 |
|   | Misc. | | PRESERVATIVES, FRAGRANCES, PH ADJUSTERS, CHELATING AGENT, ETC. | ≤2 | ≤2 | ≤2 | ≤2 | ≤2 | |
| e | | | WATER | 78 | 78 | 69 | 72 | 71 | 73 |
| Transparent | | | | Yes | Yes | No | No | No | No |

Exemplary Compositions A and B both formed a microemulsion that had a texture providing a crushed ice tactile feel. Additionally, both Exemplary Compositions A and B were transparent and exhibited minimal and/or were free of murkiness, clouding, and/or opaque clumps.

Comparative Compositions C and D had a murky appearance that included opaque/white clumps. Comparative Composition E exhibited a murky appearance. Comparative Example F also exhibited an inferior appearance as it was not transparent.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the inventive concepts as expressed herein, commensurate with the above teachings and/or the skill or knowledge of the relevant art. The embodiments described herein are further intended to explain best modes known by the applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising" and "including" are used in their open, non-limiting sense.

The terms "a," "an," and "the" are understood to encompass the plural as well as the singular. Thus, the term "a mixture thereof" also relates to "mixtures thereof." Throughout the disclosure, the term "a mixture thereof" may be used, following a list of elements or components. As an illustrated example, the disclosure may state, "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included.

Likewise, the term "a salt thereof" also relates to "salts thereof." Thus, in the illustrative example where the disclosure may refer to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included. The salts referred to throughout the disclosure may include salts having a counter-ion such as an alkali metal, alkaline earth metal, or ammonium counter-ion. This list of counter-ions, however, is non-limiting.

Other than in the operating examples, or where otherwise indicated, all numbers expressing quantities of ingredients and/or reaction conditions may be modified in all instances by the term "about," meaning within +/−5% of the indicated number.

Some of the various categories of components identified may overlap. In such cases where overlap may exist and the composition includes both components (or the composition includes more than two components that overlap), an overlapping compound does not represent more than one component. For example, a particular component may be considered both a cationic conditioning polymer and a thickening agent. If a particular composition includes both a cationic conditioning polymer and a thickening agent, a single ingredient will serve as only the cationic conditioning polymer or only the thickening agent (a single ingredients cannot serve as both the inorganic pigment and the soft focus powder).

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc. All ranges and values disclosed herein are inclusive and combinable. For examples, any value or point described herein that falls within a range described herein can serve as a minimum or maximum value to derive a sub-range, etc.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, or none of the specified material. All of the components set forth herein may be optionally included or excluded from the compositions/method/kits. When excluded, the compositions/methods/kits may be free or essentially free of the component. For example, a particular composition may be free or essentially free of alkoxylated fatty alcohols, for example, deceth-3. Likewise, a particular composition may be free or essentially free of sulfate based anionic surfactants.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A hair coloring composition in the form a transparent microemulsion, the hair coloring composition comprising:
   (a) about 0.1 to about 10 wt. % of one or more oxidative dye precursors;
   (b) about 0.1 to about 15 wt. % of one or more anionic acyl amino acid surfactants;
   (c) about 0.1 to about 15 wt. % of one or more amphoteric surfactants;
   (d) about 0.1 to about 30 wt. % of a plurality of nonionic surfactants, the plurality of nonionic surfactants comprising:
      (i) about 0.1 to about 15 wt. % of one or more alkyl polyglucosides,
      (ii) about 0.1 to about 15 wt. % of one or more sorbitan derivatives, and
      (iii) about 0.1 to about 10 wt. % of one or more polyol esters; and
   (e) water.

2. The hair coloring composition of claim 1, wherein the aclyl amino acid surfactants are chosen from acyl sarcosinates, acyl taurates, acyl glycinates, acyl glutamates, salts thereof, and a mixture thereof.

3. The hair coloring composition of claim 2, wherein the acyl amino acid surfactants are chosen from acyl glycinates.

4. The hair coloring composition of claim 3, wherein the acyl glycinates are chosen from sodium cocoyl glycinate, sodium lauroyl glycinate, sodium myristoyl glycinate, potassium lauroyl glycinate, potassium cocoyl glycinate, and a mixture thereof.

5. The hair coloring composition of claim 1, wherein the one or more amphoteric surfactants are chosen from betaines, alkyl sultaines, alkyl amphoacetates, alkyl amphoprionates, salts thereof, and a mixture thereof.

6. The hair coloring composition of claim 5, wherein the one or more amphoteric surfactants include one or more betaines.

7. The hair coloring composition of claim 6, wherein the one or more betaines are chosen from coco betaine, cocamidopropyl betaine, lauryl betaine, laurylhydroxy sulfobetaine, lauryldimethyl betaine, cocamidopropyl hydroxysultaine, behenyl betaine, capryl/capramidopropyl betaine, lauryl hydroxysultaine, stearyl betaine, and mixtures thereof.

8. The hair coloring composition of claim 1, wherein the one or more alkyl polyglucosides are chosen from lauryl glucoside, octyl glucoside, decyl glucoside, coco glucoside, caprylyl/capryl glucoside, sodium lauryl glucose carboxylate, and a mixture thereof.

9. The hair coloring composition of claim 1, wherein the one or more sorbitan derivatives are chosen from polysorbate-20 (POE(20) sorbitan monolaurate), polysorbate-21 (POE(4) sorbitan monolaurate), polysorbate-40 (POE(20) sorbitan monopalmitate), polysorbate-60 (POE(20) sorbitan monostearate), polysorbate-61 (POE(4) sorbitan monostearate), polysorbate-65 (POE(20) sorbitan tristearate), polysorbate-80 (POE(20)sorbitan monooleate), polysorbate-81 (POE(4) sorbitan monooleate), polysorbate 85 (POE(20) Sorbitan Trioleate), sorbitan isostearate, sorbitan monolaurate, sorbitan monooleate, sorbitan monopalmitate, sorbitan monostearate, sorbitan sesquioleate, sorbitan trioleate and sorbitan tristearateand a mixture thereof.

10. The hair coloring composition of claim 9, wherein the one or more sorbitan derivatives comprises polysorbate-21 (POE(4) sorbitan monolaurate).

11. The hair coloring composition of claim 1, wherein the one or more polyol esters are chosen from alkoxylated polyol esters.

12. The hair coloring composition of claim 11, wherein the alkoxylated polyol esters are chosen from pegylated derivatives of propylene glycol oleate, propylene glycol caprylate/caprate, propylene glycol cocoate, propylene glycol stearate, and a mixture thereof.

13. The hair coloring composition of claim 12, wherein the alkoxylated polyol esters are chosen from PEG-55 propylene glycol oleate, PEG-6 propylene glycol caprylate/caprate, PEG-8 propylene glycol cocoate, PEG-25 propylene glycol stearate, and PEG-120 propylene glycol stearate, and a mixture thereof.

14. The hair coloring composition of claim 1, further comprising:
   (f) one or more water-soluble solvents.

15. The hair coloring composition of claim 1, wherein the one or more water-soluble solvents are chosen from one or more glycols, $C_{1-6}$ alcohols, glycerin, and a mixture thereof.

16. The hair coloring composition of claim 15 comprising one or more glycols chosen from ethylene glycol, propylene glycol, butylene glycol, hexylene glycol, pentylene glycol, diethylene glycol, dipropylene glycol, 1,3 propanediol, glycerin, and a mixture thereof.

17. The hair coloring composition of claim 1, further comprising:

(g) one or more alkalizing agents chosen from alkali metal carbonates, alkali metal phosphates, organic amines, hydroxide base compounds, and mixtures thereof.

18. The hair coloring composition of claim 17, wherein the one or more alkalizing agents are chosen from ammonium hydroxide, ethanolamine and mixtures thereof.

19. A kit comprising:
   i. a hair coloring composition of claim 1; and
   ii. an aqueous developer composition comprising one or more peroxides.

20. A method for coloring hair comprising:
   i. mixing an aqueous developer composition comprising one or more peroxides with a hair coloring composition comprising:
      (a) about 0.1 to about 10 wt. % of one or more oxidative dye precursors,
      (b) about 0.1 to about 15 wt. % of one or more anionic acyl amino acid surfactants,
      (c) about 0.1 to about 15 wt. % of one or more amphoteric surfactants,
      (d) about 0.1 to about 30 wt. % of a plurality of nonionic surfactants, the plurality of nonionic surfactants comprising:
         (i) about 0.1 to about 15 wt. % of one or more alkyl polyglucosides,
         (ii) about 0.1 to about 15 wt. % of one or more sorbitan derivatives,
         (iii) about 0.1 to about 10 wt. % of one or more polyol esters,
      (e) water; and
   ii. applying the mixture onto hair and allowing the mixture to remain on the hair for about 1 to about 45 minutes; and
   iii. rinsing the mixture from hair.

* * * * *